United States Patent
Dalesandro et al.

(10) Patent No.: US 6,230,713 B1
(45) Date of Patent: May 15, 2001

(54) DETERMINING A TREATMENT PLAN FOR PATIENTS UNDERGOING THROMBOTIC EVENT BY MONITORING P-SELECTIN

(76) Inventors: Margaret R. Dalesandro, 610 Clovelly La., Devon, PA (US) 19333; Paul A. Gurbel, 108 St. Albans Way, Baltimore, MD (US) 21212; Victor L. Serebruany, 9101 E. Stayman Dr., Ellicott City, MD (US) 21042

(*) Notice: Subject to any disclaimer, the term of this patent is extended or adjusted under 35 U.S.C. 154(b) by 0 days.

(21) Appl. No.: 09/015,385

(22) Filed: Jan. 29, 1998

(51) Int. Cl.$^7$ .................................................. A61B 19/00
(52) U.S. Cl. ............................................ 128/898; 514/170
(58) Field of Search ..................... 514/170, 25; 128/898; 600/300; 604/500

(56) References Cited

U.S. PATENT DOCUMENTS 5,489,581 * 2/1996 Daynes et al. ........................ 514/170
5,583,126 * 12/1996 Daynes et al. ........................ 514/170
5,837,689 * 11/1998 Anderson et al. ..................... 514/25

* cited by examiner

Primary Examiner—David H. Willse
Assistant Examiner—Kelly O'Hara
(74) Attorney, Agent, or Firm—Hamilton, Brook, Smith & Reynolds, P.C.

(57) ABSTRACT

A treatment plan for patients suffering from a thrombotic event can be determined by measuring membrane bound and/or soluble P-selectin. The degree of reperfusion can be determined by assessing the level of soluble P-selectin subsequent to reperfusion. Additionally, predicting whether thrombolytic therapy will induce reperfusion can be determined by measuring the level of membrane bound P-selectin prior to reperfusion.

4 Claims, 7 Drawing Sheets

DETERMINING A TREATMENT PLAN FOR PATIENTS UNDERGOING THROMBOTIC EVENT BY MONITORING P-SELECTIN

BACKGROUND OF THE INVENTION

A thrombotic event occurs when a clot forms and lodges within a blood vessel. The clot may fully or partially block the blood vessel causing a thrombotic disorder such as a heart attack or stroke. Forms of a heart attack include angina and myocardial infarction. Often, a thrombolytic agent is used to dissolve the clot. Reperfusion occurs when the clot is dissolved and blood flow is restored.

Two phases of thrombotic events may exist, an ischemic stage and a necrotic stage. A patient may suffer from ischemia in which a decrease of blood flow may occur. This decrease in blood flow causes a decrease in tissue oxygenation. After prolonged ischemia, the tissue may undergo necrosis which is death of the tissue. Necrosis occurs in a time dependent fashion and can be prevented by the restoration of blood flow. Therefore, the ability to determine whether thrombolytic therapy will cause reperfusion prior to its administration is important. Accordingly, a need exists to predict whether a thrombolytic agent will induce reperfusion prior to its administration. Similarly, administering adequate therapy and reperfusing the patient in a timely fashion is important. Consequently, a need exists to determine the whether reperfusion has occurred within a reasonable time after a physician has administered therapy.

SUMMARY OF THE INVENTION

The present invention relates to methods, apparatuses and kits for determining and/or monitoring a treatment plan for patients suffering from a thrombotic event. This treatment plan allows a physician to determine the likelihood that a thrombolytic agent will induce reperfusion prior to its administration and, if administered, whether reperfusion has actually occurred. This method involves assessing the level of a sensitive marker for platelet activation and/or reperfusion called P-selectin.

Two forms of P-selectin exist. One form is soluble P-selectin and the other is membrane bound P-selectin. The claimed invention allows a physician to determine whether reperfusion has occurred by measuring the level of soluble P-selectin. Reperfusion can occur after thrombolytic therapy, coronary intervention, or by some other mechanism which induces reperfusion including spontaneous reperfusion. A spike, or an increase and subsequent decrease, of soluble P-selectin is indicative of successful reperfusion.

Similarly, a physician can determine whether thrombolytic therapy will induce reperfusion by assessing the level of membrane bound P-selectin. An increase in membrane bound P-selectin as compared with a standard indicates that a patient is less likely to reperfuse.

Accordingly, the claimed invention pertains to measuring both soluble and membrane bound P-selectin to allow the physician to determine a treatment plan for a patient suffering from a thrombotic event. Additionally, the claimed invention allows for determination of a clinical outcome or course based the levels of P-selectin assessed.

The claimed invention offers several advantages. The claimed invention allows a physician to monitor the patient and the efficacy of treatment. For example, the invention allows a physician to more efficiently and quickly determine a course of treatment to prevent necrosis or tissue death. Furthermore, the invention enables a physician to predict whether thrombolytic therapy will work and induce reperfusion. This information makes treatment more efficient because the physician can choose more effective methods of treatment and administer them in a timely manner.

BRIEF DESCRIPTION OF THE DRAWINGS

The foregoing and other objects, features and advantages of the invention will be apparent from the following more particular description of preferred embodiments of the invention, as illustrated in the accompanying figures. The emphasis of the figures is on illustrating the invention's principles.

FIG. 6A shows the dose-dependent increase in the binding of $^{125}$I-S12 to platelets activated by PMA ranging from 5–500 nM final concentration. FIG. 6B depicts the activation indices for platelet P selectin expression for a dose titration of PMA. The activation indices are the ratio between the endogenous P-selectin expressed and the P-selectin that could be expressed under conditions designed to stimulate expression of all available P-selectin.

FIG. 7A shows the soluble P-selectin levels in patients who adequately reperfused. FIG. 7B shows the soluble P-selectin levels in patients who did not adequately reperfuse.

FIG. 8A shows the membrane bound P-selectin levels in patients who adequately reperfused. FIG. 8B shows the membrane bound P-selectin levels in patients who did not adequately reperfuse.

DETAILED DESCRIPTION OF THE INVENTION

Figure 1:
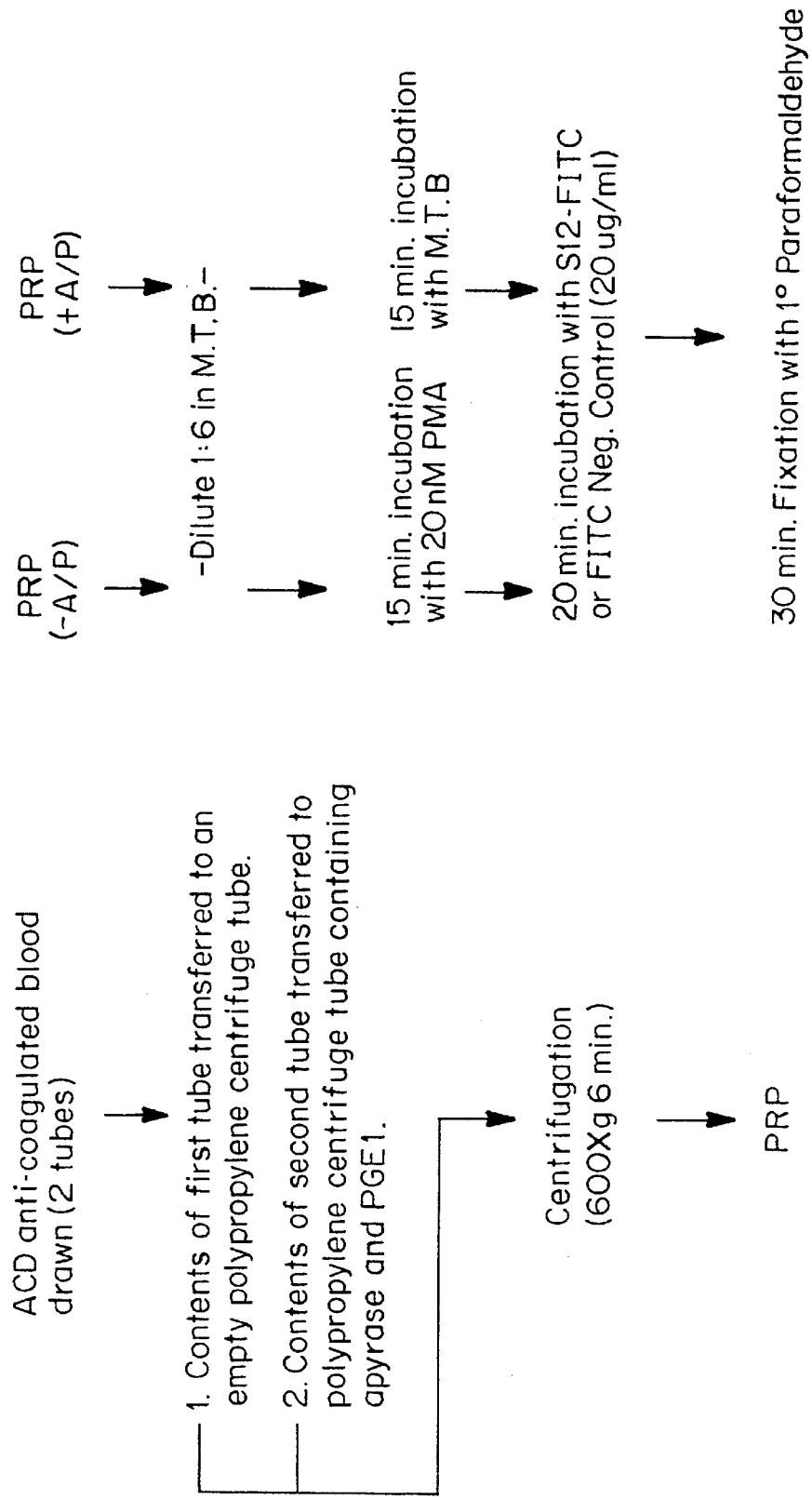
FIG. 1 is a schematic depiction illustrating a flow cytometry assay useful for the determination of membrane bound P-selectin. The following abbreviations are used in the figure which designate the various reagents utilized in the assay: ACD, Acid citrate dextrose; $PGE_1$, prostaglandin $E_1$; PRP, platelet-rich plasma; A/P, apyrase plus prostaglandin $E_1$; MTB, modified Tyrodes Buffer; FITC, fluorescein isothiocyanate, PMA, phorbol 12-myristate 13-acetate, S12-FITC, FITC-labeled anti-P-selectin monoclonal antibody (Mab) S12.

The present invention relates to a method for determining a treatment plan for patients undergoing a thrombotic event by measuring membrane bound and/or soluble P-selectin. Assessing these levels of P-selectin and comparing them with a standard allows physicians to determine an efficient course of treatment. Measuring a membrane bound P-selectin level of a patient who is suffering from a thrombotic event allows the physician to determine whether administering thrombolytic therapy will be effective. Similarly, measuring a patient's soluble P-selectin will allow a physician to determine whether reperfusion in a patient has occurred, as a result of thrombolytic therapy or some other method inducing reperfusion.

Role of Platelets and P-selectin

Platelets play a key role in thrombotic disorders including arterial thrombosis and coronary syndromes. Platelets become activated through numerous stimuli including thrombin, subendothelial interactions, contact with artificial surfaces, and in the presence of some immune complexes. Once activated, platelets expose the fibrinogen binding sites on the membrane glycoprotein GP IIb/IIIa complex and platelet aggregation takes place through fibrinogen bridging thereby allowing a clot to form.

P-selectin, also known as CD62, GMP-140, or PADGEM, is a member of the selectin family of adhesion receptors. P-selectin is an integral membrane glycoprotein found in the α granules of non-activated platelets and in the Weibel-Palade bodies of endothelial cells. Upon platelet activation, platelets degranulate and glycoproteins such as P-selectin diffuse out onto the surface where they can be detected with specific antibodies.

Membrane bound P-selectin mediates the adherence of degranulated platelets to leukocytes in vivo. Skilled artisans disagree about whether degranulated platelets are cleared from circulation or continue to circulate after platelet activation. Therefore, diagnostic and clinical uses of membrane bound P-selectin have been unclear.

Skilled artisans also disagree about the source and function of soluble P-selectin. Studies reveal that the source may be activated platelets or endothelial cells or both, and consequently, the relationship between soluble P-selectin and platelet activation has been unclear.

Definitions

This section provides some definitions which are utilized throughout the specification and in the claims. Definitions are also provided through the specification and are not limited to this section.

The term "P-selectin" includes P-selectin molecules both from platelet origin and from endothelial origin. This term includes both membrane-bound and soluble forms as well as polymorphic or allelic variants and other isoforms. P-selectin embodies forms which alternative splicing or other cellular processes may produce as well as forms which occur from proteolytic cleavage of the membrane form. This term also includes both modified and unmodified forms of the foregoing such as glycosylated and unglycosylated forms. The terms, "platelet P-selectin" and "membrane bound P-selectin" are interchangeable.

The term, "antibody," encompasses polyclonal antibodies, monoclonal antibodies, single chain antibodies, chimeric, humanized, primatized, CDR-grafted, and veneered antibodies. This term further includes portions derived from different species, human antibodies which are native or derived from combinatorial libraries, and the like. Conventional techniques can chemically join together the various portions of these antibodies. Genetic engineering techniques can also prepare the antibody as a contiguous protein. For example, nucleic acids encoding a chimeric or humanized chain can be expressed to produce a contiguous protein.

In addition, functional fragments of antibodies, including fragments of chimeric, humanized, primatized, veneered or single chain antibodies can also be produced. Functional fragments of the foregoing antibodies include those which are reactive with P-selectin. For example, the invention encompasses antibody fragments capable of binding to P-selectin or portion thereof, including, but not limited to, Fv, Fab, Fab' and F(ab')$_2$ fragments. Enzymatic cleavage or recombinant techniques can produce these functional fragments. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can include DNA sequences encoding the CH$_1$ domain and hinge region of the heavy chain.

The term "antibody" also includes various forms of modified antibodies. For example, modification may occur by directly or indirectly attaching a detectable label. The detectable labels may include a radioisotope, spin label, antigen label such as a FLAG tag, enzyme label, fluorescent or chemiluminescent group and the like.

The term "sample" means tissue, fluid, whole blood, plasma, serum and aqueous blood components from a patient. The term, sample, also includes any type of bodily substance containing activated platelets or any form of P-selectin.

The term "technician," "healthcare provider" "physician" or "researcher" refers to any person qualified or capable of obtaining a suitable sample and/or assessing the levels of P-selectin. These terms also encompass a person capable of comparing levels of P-selectin to those within normal limits to determine whether the sample levels of P-selectin are elevated. These terms are interchangeable.

The term "dual assay" or "P-selectin profile" means an assay capable of determining the levels of soluble and membrane bound P-selectin.

The term, "thrombotic event," includes, but is not limited to, thrombotic disorders such as myocardial infarction, unstable angina, stroke, pulmonary embolism, transient ischemic attack, deep vein thrombosis, thrombotic re-occlusion and peripheral vascular thrombosis. A thrombotic event also includes thrombotic re-occlusion which occurs subsequent to a coronary intervention procedure or thrombolytic therapy. The term, "thrombotic event," means any disorder which involves a blockage or partial blockage of an artery or vein with a thrombosis.

The term, "standard," refers to a control or baseline level against which assessed levels of P-selectin may be compared. A standard can be obtained from a sample of apparently healthy donors. A standard also refers to a baseline measurement which is obtained from the patient prior to administration of therapy. In some instances, a standard also refers to P-selectin measurements from a patient population that successfully or unsuccessfully reperfused.

The term, "thrombolytic agent," refers an agent which is capable of inducing reperfusion by dissolving, dislodging or otherwise breaking up a clot. Some widely used thrombolytic agents include recombinant tissue plasminogen activator (ALTEPLASE® or TPA), other forms of tissue plasminogen activator (RETEPLASE™ or RPA), streptokinase and urokinase. Thrombolytic agents also include other genetically engineered plasminogen activators.

Reperfusion can produce varying degrees of blood flow restoration. Reperfusion with a high degree of blood flow restoration refers to a patient whose blood flow is essentially fully restored, even at the microvascular level. A patient may also reperfuse with a much lower degree of blood flow restoration in which blood flow may only be partially restored, and less likely to be restored microvascularly. Therefore, adequate or successful reperfusion refers to reperfusion with a higher degree of restored blood flow whereas inadequate or unsuccessful reperfusion refers to a partial or lower degree of restored blood flow. The term, "reperfusion," also means successful reperfusion or adequate reperfusion, reperfusion that occurs with a higher degree of blood flow. Reperfusion can occur as a result of thrombolytic therapy, anti-platelet therapy, coronary intervention using catheter based methods, by spontaneous reperfusion or otherwise.

Diagnostic Applications

The invention embodies a method for determining a treatment plan for a patient suffering from a thrombotic event by measuring soluble and/or platelet bound P-selectin. Assessing levels of P-selectin at various stages or time points prior to and/or during the course of treatment provides a physician with information to make better and more efficient decisions regarding treatment.

Assessing the level of membrane bound P-selectin prior to thrombolytic therapy allows a physician to predict the likelihood or probability of successful reperfusion. An elevated level of membrane bound P-selectin prior to reperfusion as compared to a standard or control indicates that administration of a thrombolytic agent will not induce successful reperfusion. (See Example 9). An increase in platelet P-selectin appears to exist in patients who are less likely to reperfuse believed to be because the clot composition contains a higher percentage of platelets as compared to the clot composition in patients who successfully reperfused. A standard, in this instance, can be obtained from a patient population in which the platelet P-selectin level was measured in patients who successfully reperfused. Alternatively, the standard can be compared to samples from healthy controls. Therefore, based on this membrane bound P-selectin and comparison, a physician can alter the treatment plan for the patient. For example, if a patient exhibits an elevated level of platelet P-selectin then a physician can choose to perform a coronary intervention procedure rather than administering thrombolytic therapy or give a GP IIB/IIIA antagonist in combination with the thrombolytic therapy. Such a predictive marker allows a patient to receive adequate therapy earlier thereby decreasing the likelihood of serious medical consequences including permanent tissue injury or death.

Another embodiment of the invention encompasses assessing the level of soluble P-selectin to determine the degree of reperfusion. Unexpectedly, upon successful reperfusion, an increase and a subsequent decrease in the level of soluble P-selectin is observed. (See Example 9). This increase and subsequent decrease in soluble P-selectin can be characterized as a soluble P-selectin spike or peak. This soluble P-selectin spike is generally observed at temporal points from immediately after a successful reperfusion up to approximately 6 hours. Measuring soluble P-selectin at one or more temporal points after reperfusion allows a physician to ascertain whether a soluble P-selectin peak exists. Soluble P-selectin begins to rise almost immediately after reperfusion as a result of the restored blood flow. A physician can compare soluble P-selectin levels to a standard which can either be the patient's baseline level prior to reperfusion or levels from apparently healthy controls. This surprising result occurs because the restoration of the blood flow appears to cleave the membrane bound P-selectin in the lumen of the occluded vessel resulting in an increase of soluble P-selectin. It is believed that the blood flow restoration deposits the cleaved P-selectin produced by the activated endothelium as well as the cleaved and soluble P-selectin from activated platelets which were trapped in the clot. Therefore, an advantage of the claimed invention over present markers for reperfusion is that a physician can assess soluble P-selectin earlier during the course of treatment than other markers of reperfusion such as troponin (TN) or creatine phosphokinase (CPK) which peak later after reperfusion. Another advantage of the claimed invention relates to a more accurate indication of successful reperfusion. For instance, an angiography may mistakenly show adequate reperfusion. Although reperfusion occurs in the larger vessels, the angiography does not indicate reperfusion at the microvascular level. However, the claimed invention more accurately assesses reperfusion because measuring P-selectin indicates restored blood flow in both the larger vessels and microvasculature.

Using soluble P-selectin as a reperfusion marker can be used in conjunction with the results from an electrocardiogram (EKG). For example, a physician can obtain a baseline EKG prior to therapy administration to ascertain the nature and size of the infarct. The greater the number of elevated ST segments in a twelve lead EKG, for example, indicates a higher degree of myocardial injury. The size of the soluble P-selectin peak is proportional to the amount and adequacy of the reperfused myocardium. Therefore, the results from an EKG assists the physician in determine the degree of reperfusion as compared to the size and/or area of the soluble P-selectin peak. Therefore, measuring soluble P-selectin in conjunction with obtaining a baseline EKG better assists a physician in determining the adequacy or success of reperfusion.

In another aspect of the invention, a skilled artisan using known methods and practices can utilize the correlation between an EKG and soluble P-selectin levels in determining the degree of reperfusion. An algorithm or mathematical formula can assess both EKG results and soluble P-selectin levels to ascertain the degree of reperfusion.

The claimed invention also encompasses a method of determining a treatment plan by assessing both membrane bound and/or soluble P-selectin as described herein. Assessing each independently at the particular times described provides information upon which a physician can make a decision regarding treatment. Measuring both membrane bound and soluble P-selectin, referred to the P-selectin profile, at various points during treatment enables a physician to obtain clearer indications of the treatment's success. For example, assessing platelet P-selectin prior to reperfusion may indicate whether thrombolytic therapy is a preferred treatment. Continuing to measure platelet P-selectin in addition to soluble P-selectin after reperfusion will not only indicate whether the patient has reperfused, but also indicate whether additional platelet activation is occurring. An elevated level of platelet P-selectin after thrombolytic therapy indicates the need for anti-platelet therapy. Therefore, assessing levels in a P-selectin profile prior to and during the course of treatment in a patient suffering from a thrombotic event allows a physician to make better treatment decisions.

Additionally, monitoring both forms of P-selectin allows a physician to determine whether the patient has "Exhausted Platelet Syndrome." For instance, if both forms of P-selectin are low, even below control levels, then this information suggests that the patient has exhausted platelets. These low levels are also a contraindication of thrombolytic therapy. Hence, monitoring both levels of P-selectin allow a physician to monitor a patient's treatment.

Another embodiment of the claimed invention includes a method for determining a patient's clinical outcome or course. A clinical outcome refers to a patient's long term health and the probability of adverse consequence in response to the patient's illness and treatment. Often a physician will assess the patient's likelihood of experiencing another thrombotic event, reocclusion, or death. Assessing the level of soluble P-selectin after reperfusion allows a physician to determine a patient's clinical outcome. For example, a larger peak or spike of soluble P-selectin indicates a high degree of reperfusion. A larger peak also indicates that a patient is less likely to suffer from future adverse clinical outcomes such as reocculsion or other events due to absence of reperfusion such as congestive heart failure or death. Similarly, a smaller peak indicates that reperfusion occurred to a lesser degree and therefore, the patient is more likely to suffer from adverse clinical outcomes. To better assess a patient's clinical outcome, a physician can measure levels of soluble P-selectin in conjunction with the results from an EKG, as described herein. The degree of reperfusion correlates with the likelihood that a patient will suffer from adverse consequence, resulting in an adverse clinical outcome.

Imununological Assessment of P-Selectin

The claimed invention utilizes several suitable assays which can measure soluble and/or membrane bound P-selectin. Suitable assays encompass immunological methods, such as radioimmunoassay, flow cytometry, enzyme-linked immunosorbent assays (ELISA), chemiluminescence assays, and assessment with a volumetric capillary cytometry system. Any method known now or developed later can be used for performing the invention and measuring P-selectin.

The inventive methods utilize antibodies reactive with P-selectin or portions thereof. In a preferred embodiment, the antibodies specifically bind with membrane bound and/or soluble P-selectin or a portion thereof (see e.g., Furie et al., U.S. Pat. No. 4,783,330, the teachings of which are incorporated herein by reference in their entirety). The antibodies can be polyclonal or monoclonal, and the term antibody is intended to encompass polyclonal and monoclonal antibodies, and functional fragments thereof. The terms polyclonal and monoclonal refer to the degree of homogeneity of an antibody preparation, and are not intended to be limited to particular methods of production.

In several of the preferred embodiments, immunological techniques detect P-selectin levels by means of an anti-P-selectin antibody (i.e., one or more antibodies), such as monoclonal antibodies S12 or W40. The term "anti-P-selectin" antibody includes monoclonal and/or polyclonal antibodies, and mixtures thereof. For example, these immunological techniques can utilize mixtures of polyclonal and/or monoclonal antibodies, such as a cocktail of murine W40, S12 and G1 monoclonal antibodies.

A researcher can raise anti-P-selectin antibodies against an appropriate immunogen, such as isolated and/or recombinant P-selectin or portion thereof (including synthetic molecules, such as synthetic peptides). In one embodiment, antibodies are raised against an isolated and/or recombinant P-selectin or portion thereof (e.g., a peptide) or against a host cell which expresses recombinant P-selectin (Johnston, G. I. et al., *Cell*, 56: 1033–1044 (1989); and McEver, R. P., U.S. Pat. No. 5,378,464, the teachings of which are both incorporated herein by reference in their entirety). In addition, cells expressing recombinant P-selectin, such as transfected cells, can be used as immunogens or in a screen for antibody which binds receptor (See e.g., Chuntharapai et al., *J. Immunol.*, 152: 1783–1789 (1994); Chuntharapai et al., U.S. Pat. No. 5,440,021).

Any suitable technique can prepare the immunizing antigen and produce polyclonal or monoclonal antibodies. The prior art contains a variety of these methods (see e.g., Kohler et al., *Nature*, 256: 495–497 (1975) and *Eur. J. Immunol.* 6: 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual*, (Cold Spring Harbor Laboratory: Cold Spring Harbor, N.Y.); *Current Protocols In Molecular Biology*, Vol. 2 (Supplement 27, Summer '94), Ausubel, F. M. et al., Eds., (John Wiley & Sons: New York, N.Y.), Chapter 11, (1991)). Generally, fusing a suitable immortal or myeloma cell line, such as SP2/0, with antibody producing cells can produce a hybridoma. Animals immunized with the antigen of interest provide the antibody producing cell, preferably cells from the spleen or lymph nodes. Selective culture conditions isolate antibody producing hybridoma cells while limiting dilution techniques produce them. Researchers can use suitable assays such as ELISA to select antibody producing cells with the desired specificity.

Other suitable methods can produce or isolate antibodies of the requisite specificity. Examples of other methods include selecting recombinant antibody from a library or relying upon immunization of transgenic animals such as mice which are capable of producing a full repertoire of human antibodies (see e.g., Jakobovits et al., *Proc. Natl. Acad. Sci. USA*, 90: 2551–2555 (1993); Jakobovits et al., *Nature*, 362: 255–258 (1993); Lonberg et al., U.S. Pat. No. 5,545,806; Surani et al., U.S. Pat. No. 5,545,807).

According to the method, an assay can determine the level of P-selectin in a biological sample. In determining the amounts of membrane bound and/or soluble P-selectin, an assay includes combining the sample to be tested with an antibody having specificity for P-selectin, under conditions suitable for formation of a complex between antibody and P-selectin, and detecting or measuring (directly or indirectly) the formation of a complex. The sample can be obtained and prepared by a method suitable for the particular sample (e.g., whole blood, platelet rich plasma, platelet poor plasma, serum) and assay format selected. For example, suitable methods for whole blood collection are venipuncture or obtaining blood from an in-dwelling arterial line. The container into which a healthcare provider deposits the blood can contain an anti-coagulant such as CACD-A, heparin, or EDTA. Methods of combining sample and antibody, and methods of detecting complex formation are also selected to be compatible with the assay format. Suitable labels can be detected directly, such as radioactive, fluorescent or chemiluminescent labels. They can also be indirectly detected using labels such as enzyme labels and other antigenic or specific binding partners like biotin. Examples of such labels include fluorescent labels such as fluorescein, rhodamine, CY5, APC, chemiluminescent labels such as luciferase, radioisotope labels such as $^{32}P$, $^{125}I$, $^{131}I$, enzyme labels such as horseradish peroxidase, and alkaline phosphatase, β-galactosidase, biotin, avidin, spin labels and the like. The detection of antibodies in a complex can also be done immunologically with a second antibody which is then detected. Conventional methods or other suitable methods can directly or indirectly label an antibody.

Assaying for Detection of Membrane Bound P-selectin and Total Platelet Count

Any method known now or developed later can be used for measuring membrane bound P-selectin. One method for assessing membrane bound P-selectin levels which the invention utilizes is flow cytometry. Methods of flow cytometry for measuring platelet or membrane bound P-selectin are well know in the art. (Shattil, Sanford J, et al. "Detection of Activated Platelets in Whole Blood using Activation-Dependent Monoclonal Antibodies and Flow Cytometry," *Blood*, Vol. 70, No 1 (July), 1987: pp307–315; Scharf, Rudiger E., et al., "Activation of Platelets in Blood Perfusing Angioplasty-damaged Coronary Arteries, Flow Cytometric Detection," *Arteriosclerosis and Thrombosis*, Vol 12, No 12 (December), 1992: pp 1475–1487, the teachings of which are incorporated herein by reference in their entirety). Also, the teachings of co-pending applications, Ser. No. 08/748,387, filed Nov. 13, 1996, entitled "Assessment of P-selectin in Venous Thrombotic Disorders, Vascular Interventions and Monitoring of Anti-Platelet Therapy," and PCT application number PCT/US97/20571, filed Nov. 13, 1997, entitled, "P-Selectin Assays and Methods of Use Thereof," are incorporated herein by reference in their entirety.

For example, a sample comprising platelets can be contacted with an antibody having specificity for P-selectin under conditions suitable for formation of a complex between an antibody and P-selectin expressed on platelets, and detecting or measuring (directly or indirectly) the formation of a complex. In a particularly preferred embodiment, the antibody, S-12 is conjugated with FITC. FIG. 1 illustrates one type of flow cytometry assay. (see also Example 4).

For example, the level of membrane bound P-selectin can be assessed by flow cytometry comprising:
 (a) obtaining a first and second sample comprising platelets,
 (b) contacting said first sample, serving as a control, with a platelet activation agonist, such as phorbol myristate acetate (PMA), ADP (adenosine diphosphate), thrombin, collagen, and/or TRAP (thrombin receptor activating peptide), under conditions suitable for activation of platelets in said first sample, preferably for a period of time effective to maximally activate said platelets, and preferably while maintaining the second sample under conditions suitable for maintaining the endogenous platelet activation level;
 (c) contacting or staining the samples with a composition comprising an anti-P-selectin antibody, such as an anti-P-selectin antibody comprising a fluorescent label, preferably in an amount in excess of that required to bind the P-selectin expressed on the platelets, under conditions suitable for the formation of labeled complexes between said anti-P-selectin antibody and activated platelets; and
 (d) determining (detecting or measuring) the formation of complex in said samples, wherein the amount of complex detected indicates the extent of platelet activation in said second sample.

In addition to using flow cytometry to measure membrane bound P-selectin, a radioimmunoassay can also be employed and is fully described in co-pending application, Ser. No. 08/748,387, filed Nov. 13, 1996, entitled "Assessment of P-selectin in Venous Thrombotic Disorders, Vascular Interventions and Monitoring of Anti-Platelet Therapy," the teachings of which are incorporated by reference in their entirety.

Figure 2:
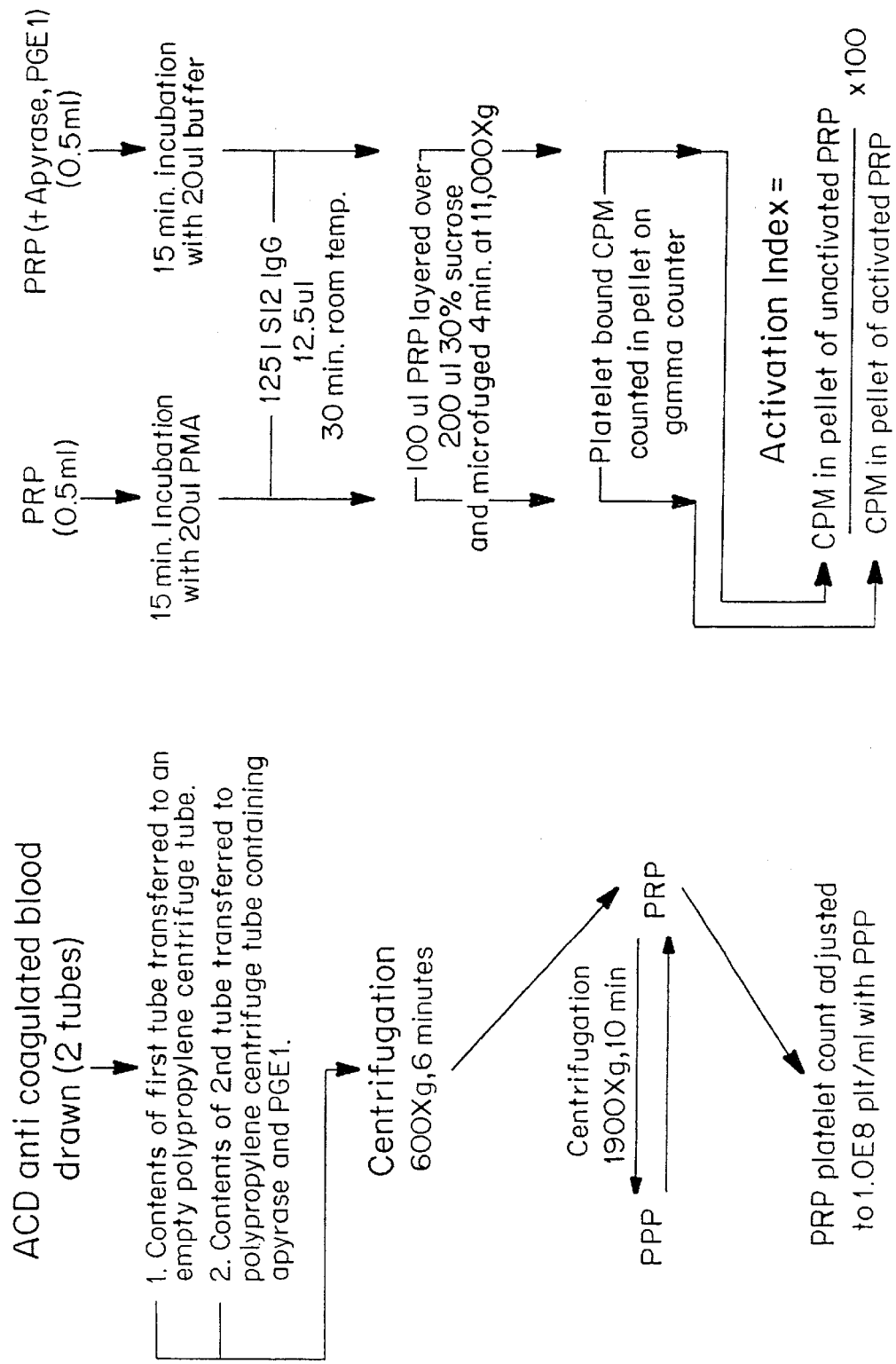
FIG. 2 is a schematic depiction illustrating a radioimmunoassay useful for the determination of membrane bound P-selectin. The following abbreviations are used in the figure which designate the various reagents utilized in the assay: ACD, Acid citrate dextrose; CPM, Counts Per Minute; $PGE_1$, prostaglandin $E_1$; PRP, platelet-rich plasma; PPP, platelet poor plasma; PMA, phorbol myristate acetate; $^{125}$I-S12 IgG, $^{125}$I-labeled anti-P-selectin monoclonal antibody (Mab) S12.

A radioimmunoassay is schematically illustrated in FIG. 2. (Also see Examples 1 and 3). For example, endogenous platelet activation can be assessed by an immunobinding assay comprising:
 (a) obtaining a first and second sample comprising platelets, wherein each sample contains a preselected number of platelets;
 (b) contacting said first sample with a platelet activation agonist, such as phorbol myristate acetate (PMA), ADP (adenosine diphosphate), thrombin, collagen, and/or TRAP (thrombin receptor activating peptide), under conditions suitable for activation of platelets in said first sample, preferably for a period of time effective to maximally activate said platelets, and preferably while maintaining the second sample under conditions suitable for maintaining the endogenous platelet activation level;
 (c) contacting said samples with a composition comprising an anti-P-selectin antibody, such as
  (i) an anti-P-selectin antibody comprising a radioactive label; or
  (ii) an anti-P-selectin antibody comprising a binding site for a second antibody which comprises a radioactive label, preferably in an amount in excess of that required to bind the P-selectin expressed on the platelets, under conditions suitable for the formation of labeled complexes between said anti-P-selectin antibody and activated platelets; and
 (d) determining (detecting or measuring) the formation of complex in said samples, wherein the amount of complex detected in said second sample as compared to that detected in said first sample is indicative of the extent of platelet activation in said second sample.

For example, a ratio reflecting the amount of complex detected in said second sample to that detected in said first sample can provide a measure of the extent of platelet activation in said second sample. Formation of complex can be assessed by determining the radioactivity present in the labeled complexes in each sample, wherein a ratio of the radioactivity of the second sample to the first sample provides a measure of the extent of platelet activation in said second sample.

Preferably, the first and second samples are from the same donor and are collected at about the same time (e.g., obtained by dividing a sample from a donor, obtained from two samples collected in series).

The assay can also be performed on whole blood without a pre-isolation step or standardization of platelet number, thus substantially reducing processing time. For example, a sample of whole blood can be obtained from a donor whose level of platelet activation is to be determined and can be divided into two portions. One sample can be treated with a platelet agonist such as PMA to maximally activate platelets, while the other sample is not treated with activation agonists, but is maintained under conditions designed to maintain the endogenous (in vivo) activation level (e.g., by addition of activation inhibitors such as aprotinin, theophylline, apyrase and/or prostaglandin $E_1$). Radioactively labeled anti-P-selectin antibody is added to both samples and samples are maintained under conditions suitable for specific binding to P-selectin, and preferably until binding is complete. The extent of binding is then assessed. The samples can be processed to separate complexes from unbound anti-P-selectin antibody. For example, samples can be diluted 1:6 with a buffer that does not alter platelet activation state, such as Tyrode's Modified Buffer, layered over a 30% sucrose barrier (e.g., in preloaded microfuge tubes), and microfuged (e.g., for 4 minutes at 11,000×g). The pellet with its bound radiolabeled anti-P-selectin antibody can be clipped and counted in a gamma counter. The percent of radioactivity in the endogenously activated sample compared with the maximally activated sample can be calculated and described as the Activation Index (AI) for the sample. In this manner, endogenous platelet activation can be measured as percent of total expressible P-selectin.

Figure 3:
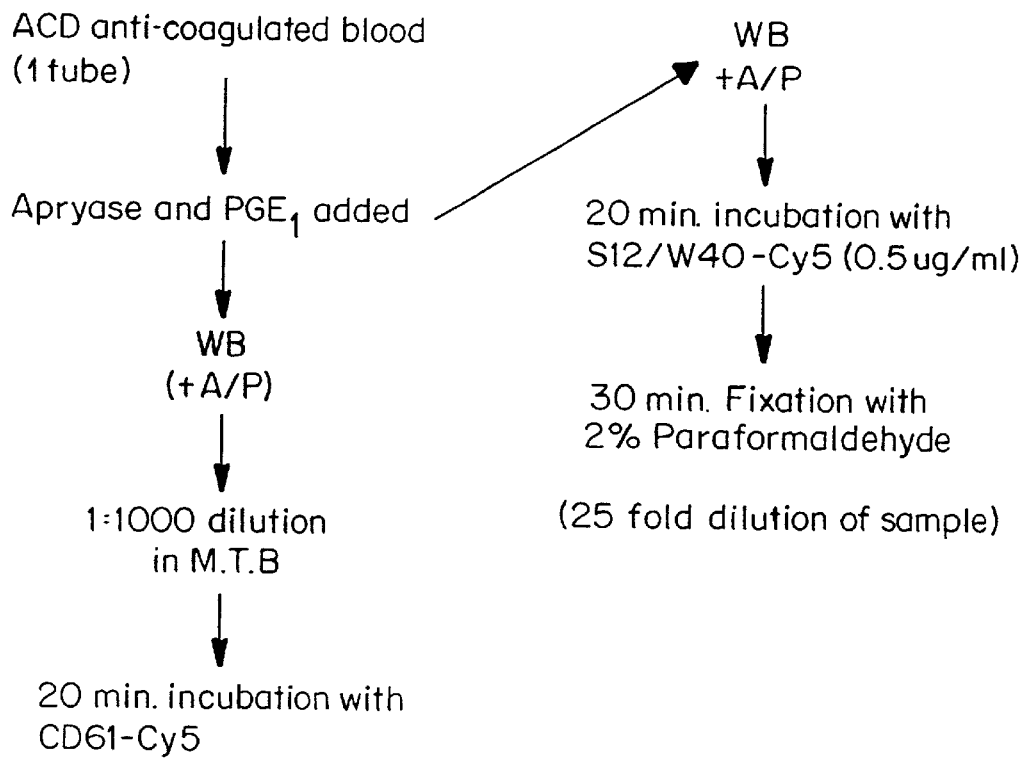
FIG. 3 is a schematic depiction illustrating a volumetric capillary cytometry system useful for the determination of membrane bound P-selectin. The volumetric capillary cytometry system is called IMAGN2000™, from Biometric Imaging, Mountain View, Calif. The following abbreviations are used in the figure which designate the various reagents utilized in the assay: ACD, Acid citrate dextrose; $PGE_1$, prostaglandin $E_1$; WB, whole blood; A/P, apyrase plus prostaglandin $E_1$; MTB, modified Tyrodes Buffer; CD61-Cy5, Cy5-labeled Mab that binds a receptor found on essentially all platelets; S12/W40-Cy5, a mixture of equal parts of Cy5-labeled anti-P-selectin Mabs S12 and W40.

Another method of assaying levels of membrane bound P-selectin involves analysis with a volumetric capillary cytometry system. An example of a volumetric capillary cytometry system is IMAGN2000™ from Biometric Imaging, Mountain View, Calif. As described in FIG. 3 and Example 5, membrane bound P-selectin is measured using a P-selectin specific antibody or mixture thereof. Preferably, the antibody is labeled with a fluorophore. More preferably, the antibodies used are a mixture or cocktail of S-12 and W-40 each of which are labeled with fluorophore, Cy-5 (Amersham-Searle) or APC/Prozyme. The volumetric capillary cytometry system detects the number of events and the fluorescent intensity.

For example, the level of membrane bound P-selectin can be assessed by a volumetric capillary cytometry system comprising:

(a) obtaining a sample comprising platelets,
(b) contacting said sample with a stabilizing reagent, such as Apyrase and Prostaglandin E1, to prevent in vitro platelet activation and stabilize the P-selectin expressed on the platelets to obtain a measure of in vivo platelet activation,
(c) contacting or staining said samples with a composition comprising an anti-P-selectin antibody, such as an anti-P-selectin antibody comprising a fluorescent label, preferably in an amount in excess of that required to bind the P-selectin expressed on the platelets, under conditions suitable for the formation of labeled complexes between said anti-P-selectin antibody and activated platelets; and
(d) determining (detecting or measuring) the formation of complex in said samples, wherein the amount of complex detected indicates the level of membrane bound P-selectin in the sample.

Assessing the total platelet count aids in determining the extent of platelet activation and therefore, the total platelet count is preferably measured in addition to membrane bound P-selectin. The total platelet count is measured by contacting the sample with an antibody specific to essentially all platelets, and then detecting the number of events or fluorescence. Preferably, the antibody is an antibody specific for a receptor existing on essentially all platelets, such as glycoprotein GP IIb/IIIa, CD61, CD41 and CD42. These antibodies are labeled with a fluorophore, namely Cy-5. (Amersham-Searle).

For example, a volumetric capillary cytometry system can assess the total platelet count in a method comprising:

(a) obtaining a sample comprising platelets,
(B) contacting or staining said samples with a composition comprising an anti-platelet antibody, such as an anti-GP IIB/IIIa antibody having a fluorescent label, preferably in an amount in excess of that required to bind the platelets, under conditions suitable for the formation of labeled complexes between said anti-platelet antibody and platelets; and
(d) determining (detecting or measuring) the formation of complex in said samples, wherein the amount of complex detected indicated the total platelet count in the sample.

Assaying for Detection of Soluble P-selectin

Figure 4:
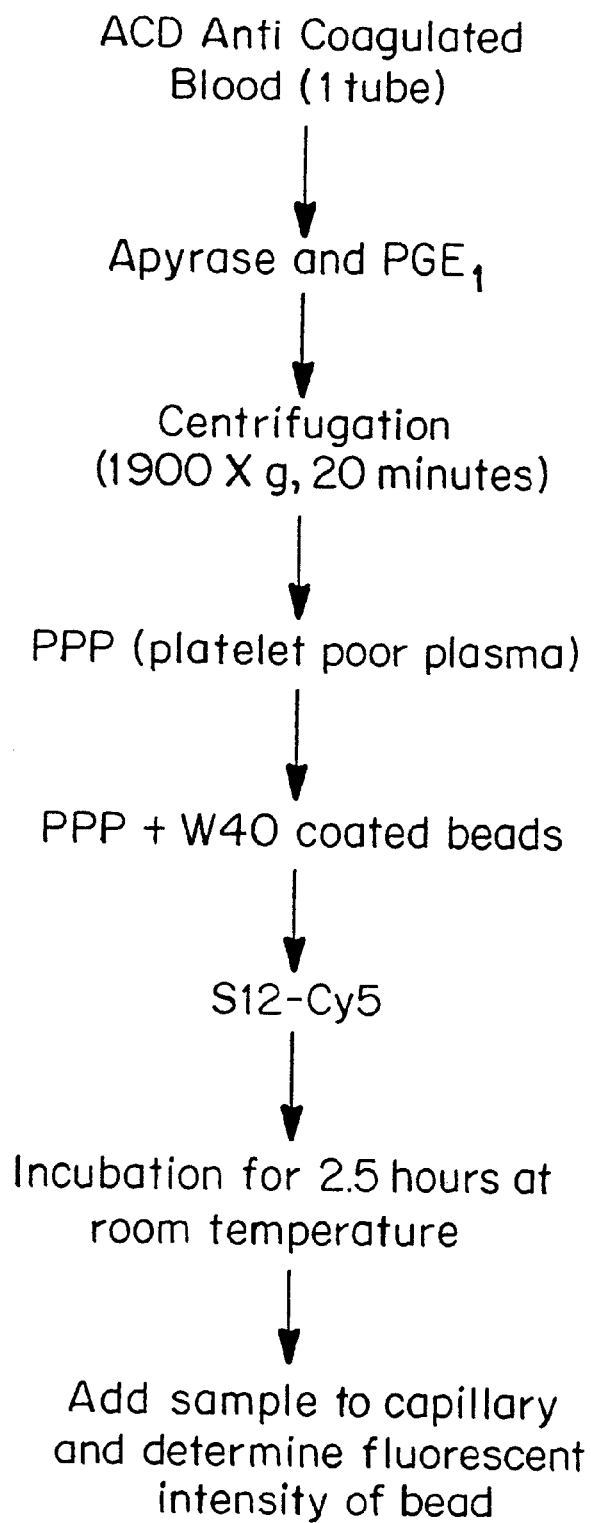
FIG. 4 is a schematic depiction illustrating a volumetric capillary cytometry system useful for the determination of soluble P-selectin in plasma from a patient sample. The following abbreviations are used in the figure which designate the various reagents utilized in the assay: ACD, acid citrate dextrose, A/P, apyrase plus prostaglandin $E_1$ PPP, platelet poor plasma, W40, P-selectin specific Mab used to coat 9.7 μM polystyrene particles; S12-Cy5, Cy5-labeled P-selectin specific Mab.

The invention can use any method known now or developed later to measure soluble P-selectin. In a preferred embodiment, soluble P-selectin is determined using an ELISA assay or a sandwich ELISA assay. In a preferred embodiment, the volumetric capillary cytometry system measures the level of soluble P-selectin. FIG. 4 illustrates one type of assay which a volumetric capillary cytometry system can perform (see also Example 6). In one embodiment, murine W40 is used as capture antibody and murine S12 is used as detector antibody.

For detection of soluble P-selectin in a suitable sample, a sample (e.g., blood) is collected, and preferably platelets are removed (partially or completely) from the sample, for example by preparation of serum or plasma (e.g., isolation of platelet poor plasma). Samples are preferably processed to remove platelets within a time suitable to reduce artificial increases in soluble P-selectin, such as those due to production of additional P-selectin (e.g., by secretion or proteolysis from platelets). For example, initiation of such processing within about one hour, and preferably immediately, is desirable. Samples can be further processed as appropriate (e.g., by dilution with assay buffer (e.g., ELISA diluent)). Additionally, the technician can add a reagent which stabilizes and prevents in vitro platelet activation. Examples of these stabilizing reagents are apyrase and $PGE_1$.

To determine a measurement for soluble P-selectin using an ELISA assay in a suitable sample such as serum, platelet poor plasma (PPP), the method comprises:

(a) combining
   (i) a suitable sample,
   (ii) a composition comprising an anti-P-selectin antibody as detector, such as
      (a) biotinylated anti-P-selectin MAb (e.g., S12) and HRP-streptavidin, or
      (b) HRP-conjugated anti-P-selectin Mab, and
   (ii) a solid support, such as a microtiter plate, having an anti-P-selectin capture antibody bound (directly or indirectly) thereto, wherein the detector antibody binds to a different P-selectin epitope from that recognized by the capture antibody, under conditions suitable for the formation of a complex between said anti-P-selectin antibodies and soluble P-selectin; and (b) determining the formation of complex in said samples.

The solid support, such as a microtiter plate, dipstick, bead, or other suitable support, can be coated directly or indirectly with an anti-P-selectin antibody. For example, an anti-P-selectin antibody can coat a microtiter well, or a biotinylated anti-P-selectin Mab can be added to a streptavidin coated support. A variety of immobilizing or coating methods as well as a number of solid supports can be used, and can be selected according to the desired format.

In a preferred embodiment, the sample or soluble P-selectin standard is combined with the solid support simultaneously with the detector antibody, and optionally with a one or more reagents by which detection is monitored. For example, the sample such as PPP can be combined with the solid support simultaneously with (a) HRP-conjugated anti-P-selectin Mab, or (b) a biotinylated anti-P-selectin Mab and HRP-streptavidin.

A known amount of soluble P-selectin standard can be prepared and processed as described above for a suitable sample. This soluble P-selectin standard assists in quantifying the amount of P-selectin detected by comparing the level of P-selectin in the sample relative to that in the standard. In one embodiment, soluble truncated P-selectin is used as a standard.

A physician, technician, apparatus or a qualified person can compare the amount of detected complex with a suitable control to determine if the levels are elevated. For example, the level of soluble P-selectin following a vascular intervention procedure can be compared with a basal level for the individual such as a level determined prior to or at the time of the procedure, or with levels in normal individuals or suitable controls.

In one embodiment of the invention, the assay can be performed on serum isolated from whole blood of a donor which is allowed to clot in the absence of an anticoagulant with or without a clot-promoting gel. For example, a technician can collect whole blood in a vacutainer without anticoagulant which may or may not have a clot-promoting gel plug that separates serum. After the blood clots, a technician can remove or harvest the serum from the top of the clotted cell pellet. The technician can either assay the serum immediately thereafter in the ELISA format described above or freeze the serum at −70° C. for later analysis. In the process of clotting, platelet microparticles are released which may be expressing P-selectin on their surface. Ultracentrifugation of serum at 107,000×g for 3 hours showed that microparticle-bound P-selectin was not detected in the soluble P-selectin ELISA format described (Table 1). As seen in Table 1, the amount of soluble P-selectin detected in serum remained essentially unchanged after the sample was subjected to ultracentrifugation, a regimen which would remove microparticles from the serum. Therefore, the ELISA measures only soluble P-selectin in serum. In this assay, the mean amount of soluble P-selectin in serum is elevated over that observed in plasma (Table 1).

TABLE 1

Ultracentrifugation which removes microparticles does not significantly alter soluble P-selectin detected in the W40-S12 Mab ELISA

| Donor | Anticoagulant | Before 3 hour 107,000 × g centrifugation (soluble P-selectin ng/ml) | After 3 hour 107,000 × g centrifugation (soluble P-selectin ng/ml) |
| --- | --- | --- | --- |
| 1 | Serum with gel | 138.2 | 132.1 |
| 1 | Serum without gel | 145.0 | 134.7 |
| 1 | Plasma (ACD-A) | 40.3 | 38.4 |
| 2 | Serum with gel | 134.0 | 139.2 |
| 2 | Serum without gel | 107.2 | 102.8 |
| 2 | Plasma (ACD-A) | 45.2 | 46.36 |

Table 1 shows that ultracentrifugation at 107,000 × g for 3 hours does not change the detection of P-selectin in the soluble P-selectin ELISA for plasma or serum. These results indicate that microparticles which would be removed by ultracentrifugation are not being detected in the soluble P-selectin ELISA, but that only plasma P-selectin is being detected.
Abbreviation: ACD-A, Acid citrate dextrose, solution A.

Thus, in a preferred embodiment, the assay for measuring soluble P-selectin in a suitable sample comprises the following steps:

(a) obtaining a suitable sample such as plasma or serum;

(b) coating a microtiter plate with an anti-P-selectin capture antibody (e.g., W40) or adding a biotinylated anti-P-selectin capture antibody (e.g., W40) to a streptavidin coated solid support such as a microtiter plate;

(c) adding, preferably simultaneously, to said microtiter plate the sample to be tested (e.g., final dilution 1:4 with ELISA diluent) and a composition comprising a detector antibody and optionally a reagent for detection, such as (i) HRP-conjugated anti-P-selectin detector antibody (e.g., HRP-S12), or (ii) a composition comprising biotinylated anti-P-selectin detector antibody (e.g., biotinylated Mab S12) and HRP-streptavidin, wherein the anti-P-selectin detector antibody binds to a different P-selectin epitope from that bound by the capture antibody, and incubating same under conditions suitable for the formation of a complex between said anti-P-selectin antibodies and soluble P-selectin, preferably under conditions which maximize binding;

(d) separating complexes comprising capture antibody, soluble P-selectin and detector antibody (e.g., by washing); and (e) determining the amount of soluble P-selectin in said complexes.

Typical assays for P-selectin are sequential assays in which a plate is coated with first antibody, plasma is added, the plate is washed, second tagged antibody is added, and the plate is washed and bound second antibody is quantified. However, binding kinetics revealed that in a simultaneous format, the off-rate of the second antibody was decreased and the assay was more sensitive. Thus, a simultaneous format in which the solid support is coated with a capture antibody (e.g., W40), and plasma and detector antibody (e.g., S12) are added simultaneously, can achieve enhanced sensitivity and is preferred.

A variety of methods can determine the amount of soluble P-selectin in complexes. For example, when HRP is used as a label, a suitable substrate such as OPD can be added to produce color intensity directly proportional to the bound anti-P-selectin Mab (assessed e.g., by optical density), and therefore to the soluble P-selectin in the sample.

A technician, physician, qualified person or apparatus can compare the results to a suitable control such as a standard, levels of P-selectin in normal individuals, and baseline levels of P-selectin in a sample from the same donor. For example, the assay can be performed using a known amount of soluble P-selectin standard in lieu of a sample, and a standard curve established. One can relatively compare known amounts of the soluble P-selectin standard to the amount of complex formed or detected.

The volumetric capillary cytometry system also measures soluble P-selectin. (Illustrated in FIG. 4). The antibody detection concepts used in the ELISA and sandwich ELISA as described above apply to measurements obtained from using the volumetric capillary cytometry system. The above ELISA methods described can be adapted so that the support surface and method of detection utilized is suitable for measurement with a volumetric capillary cytometry system.

As described above, a technician obtains a suitable sample. Samples are processed to remove platelets within a suitable time, preferably within one hour, to reduce artifactual increases in soluble P-selectin, such as those due to production of additional P-selectin. Additionally, the technician can add a reagent which stabilizes and prevents in vitro platelet activations. Examples of these stabilizing reagents are apyrase and $PGE_1$. An antibody specific to P-selectin is coated or immobilized on a support surface, such as a bead, solid support strip, or modified capillary surface. The sample is contacted with the coated surface. The coated antibody is preferably W40. This coated antibody may be detectably labeled. In the preferred embodiment, a fluorofore such as Cy5 or APC labels the coated antibody. Alternatively, another antibody specific to P-selectin or a complex between P-selectin and the coated antibody can contact the sample. This second antibody is detectably labeled with a fluorofore such as Cy5 or APC. The volumetric capillary cytometry system can then determine the fluorescent intensity as a measure of soluble P-selectin.

Thus, in a preferred embodiment, the assay used in conjunction with the volumetric capillary cytometry system for measuring soluble P-selectin in a suitable sample comprises the following steps:

(a) obtaining a suitable sample, for example plasma;

(b) coating a support surface with an anti-P-selectin capture antibody (e.g., W40) or adding a biotinylated anti-P-selectin capture antibody (e.g., W40) to a streptavidin coated solid support;

(c) adding, preferably simultaneously, the sample to be tested and a composition comprising a detector antibody and a reagent for detection, such as a fluorophore (e.g., Cy5-S12) wherein the anti-P-selectin detector antibody binds to a different P-selectin epitope from that bound by the capture antibody, and incubating under conditions suitable for the formation of a complex between said anti-P-selectin antibodies and soluble P-selectin, preferably under conditions which maximize binding; and (D) determining the amount of soluble P-selectin in said complexes using a volumetric capillary cytometry system or a similar apparatus.

The P-selectin profile as a measurement of platelet activation comprises the individual determinations of the level of platelet membrane bound P-selectin and the level of soluble P-selectin in a sample. Accordingly, the individual results of the methods discussed in this document can be combined to determine the P-selectin profile. The same kit or apparatus may utilize these methods to determine the measurement of the P-selectin profile.

Exemplification:

The following Examples illustrate the claimed invention and are not intended to be limiting in any way:

EXAMPLE 1

Radioimmunoassay (RIA) for the Detection of Platelet Bound P-selectin and Platelet Activation The radioimmunoassay method used in these in vitro and in vivo studies is described schematically in FIG. 2. As shown therein, the method can be used to determine the level of platelet activation by measuring the expression of platelet-bound P-selectin. In vitro and in vivo determinations of platelet bound P-selectin described in some of the examples were performed according to the following protocol.

For in vitro studies and some in vivo studies, whole blood (8.5 cc) was collected by venipuncture using a 19-gauge needle in two 10-ml vacutainer tubes containing ACD-A (1.5 cc) as anticoagulant. If the patient had an arterial catheter in place, then blood was collected from the in-dwelling arterial line into two plastic syringes containing 1.5 cc ACD-A anticoagulant. In this latter case, each syringe was filled to the 10 cc mark (8.5 cc draw).

The blood with anticoagulant from one vacutainer or syringe was immediately transferred into a polypropylene centrifuge tube (15 ml) containing one premeasured aliquot of apyrase (final concentration 1 U/mL)(Sigma, St. Louis, Mo., Catalog No. A 9149) and prostaglandin $E_1$ ($PGE_1$, final concentration 1 $\mu$M)(Sigma, St. Louis, Mo., Catalog No. P 5515). Apyrase and $PGE_1$ prevent in vitro platelet activation and stabilize the P-selectin expressed on platelets so that the P-selectin expressed on platelets in this blood sample represents the actual in vivo level of platelet activation. Blood from the second vacutainer or syringe was immediately transferred into an empty polypropylene centrifuge tube (15 ml) and was subsequently treated with a platelet agonist to establish maximal P-selectin expression for the donor. Platelet rich plasma (PRP) was prepared from whole blood by centrifugation of both polypropylene tubes for 6 minutes at 600×g. The yellow supernatant PRP was removed from each of the tubes (with or without apyrase and $PGE_1$) with plastic pipettes and placed into empty polypropylene tubes.

Platelet poor plasma (PPP) was prepared by centrifuging (10 minutes at 1900×g) the red cell pellet remaining in the polypropylene centrifuge tube after the preparation of PRP. Platelet counts in PRP were determined using a Coulter counter and the final platelet concentration was adjusted to $1.0 \times 10^8$ platelets/mL using the appropriate PPP (i.e., with apyrase and $PGE_1$ or without apyrase and $PGE_1$).

Platelet bound P-selectin expression was measured in a radioimmunoassay (RIA) using an $^{125}$I-labeled murine anti-human P-selectin monoclonal antibody (MAb) designated S12. The S12 monoclonal antibody, which is specific for P-selectin, reacts minimally with unstimulated human platelets, but binds extensively to platelets after activation with thrombin (McEver, R. P and M. N. Martin, "A Monoclonal Antibody to a Membrane Glycoprotein Binds Only to Activated Platelets", *J. Biol. Chem.*, 259 (15): 9799–9804 (1984), the teachings of which are incorporated herein by reference in their entirety). In the RIA, the binding of $^{125}$I-labeled anti-P-selectin monoclonal antibody S12 to: (1) P-selectin molecules expressed on the surface of unstimulated platelets (treated with apyrase and $PGE_1$ to maintain in vivo P-selectin expression), and (2) P-selectin molecules expressed on the platelets of the same donors after stimulation with a final concentration of 0.5 μM phorbol myristate acetate (PMA)(Sigma, St. Louis, Mo., Catalog No. P 8139) (no apyrase or $PGE_1$), which causes maximal P-selectin expression on platelets, was determined.

To perform the RIA, Mab S12 was radioiodinated as described previously (Wagner, C. et al., *Blood*, 88: 907 (1996), the teachings of which are incorporated herein by reference in their entirety). One 0.5 ml aliquot of PRP adjusted to $1.0 \times 10^8$ platelets/ml containing apyrase and $PGE_1$ was transferred to a polypropylene microfuge tube (500 μl capacity) containing 20 μl of Modified Tyrodes Buffer (MTB), while a second 0.5 ml aliquot of PRP (without apyrase or $PGE_1$) was transferred to a similar microfuge tube containing 20 μl of PMA (final concentration in the PRP of 0.5 μM). Both tubes were gently inverted and incubated for 15 minutes at room temperature.

$^{125}$I-labeled anti-P-selectin Mab S12 (final concentration 2 μg/ml in the PRP) was added to each microfuge tube, and the tubes were incubated for 30 minutes at room temperature. Specific activity was typically in the range of 2 to 4 μCi/μg. Aliquots (100 μl) of PRP were removed from each microfuge tube and layered over 30% sucrose (200 μl)(J. T. Baker, Phillipsburg, N.J., Catalog No. 4097-04) preloaded in slender (400 μl) polypropylene microfuge tubes. Samples were microfuged for 4 minutes at 11,000×g causing the platelets with their bound $^{125}$I-S12 to pellet, and to be separated from the free $^{125}$I-S12 by the sucrose barrier. The platelet pellet was separated from the supernatant, containing free $^{125}$I-labeled anti-P-selectin Mab S12, by clipping off the bottom of the microfuge tube and determining the bound counts per minute (cpm) on a gamma counter.

An Activation Index (AI) was calculated for each donor/patient. The activation index is the percent of total P-selectin (determined in the PMA activated sample) which is expressed by the platelets in the ex vivo sample (endogenous platelet activation).

$$\text{Activation Index} = \frac{\text{cpm in pellet of ex vivo } PRP}{\text{cpm in pellet of } PMA \text{ activated } PRP} \times 100$$

The activation index (AI) calculated for eight (n=8) normal donors was 2.7±1.5.

EXAMPLE 2

Measurement of Soluble P-selectin by ELISA

The ELISA method used in these in vi tro and in vivo studies is described above. As shown herein, the method can be used to determine the level of soluble P-selectin in a sample. In vitro and in vivo determinations of soluble P-selectin described in some of the examples were performed according to the ELISA protocol described below.

Selection of Antibodies for ELISA

To select monoclonal antibodies for a sandwich ELISA, the antigen binding kinetics of three anti-P-selectin murine monoclonal antibodies (W40, S12, and G1) were examined on the BIAcore™ instrument (Pharmacia Biosensor, Uppsala Sweden), a surface plasmon resonance detection system which is applied to kinetic, binding site and concentration analysis. Each monoclonal antibody was captured on a BIAcore™ chip with a rabbit anti-mouse Fc specific antibody. Soluble P-selectin was passed over the chip, and increasing mass (indicative of the antibody on-rate) was measured. After antigen saturation had been attained, buffer was passed over the chip and antigen off-rate was seen as decreasing mass. Association rates for each of the monoclonal anti-P-selectin antibodies were equivalent, while off-rates differed significantly. Both S12 and G1 antibodies immediately exhibited fast dissociation of antigen (off-rate). In contrast, W40 did not show a loss of P-selectin when flow of antigen was replaced with buffer alone. Thus, the BIAcore™ results demonstrated a much slower off-rate of soluble P-selectin from W40 than from either S12 or G1 monoclonal antibodies.

BIAcore™ experiments also revealed that the off-rate of soluble P-selectin from S12 was unexpectedly altered when P-selectin was bound with W40 antibody. When S12 was coated on a BIAcore™ chip and soluble P-selectin was bound to saturation, soluble P-selectin was immediately released when antigen flow was discontinued. However, when W40 was used to capture soluble P-selectin on the chip and S12 was allowed to bind to the captured soluble P-selectin, S12 remained attached when buffer was passed over the chip. The off-rate of S12 from soluble P-selectin was decreased when P-selectin was captured by W40.

Accordingly, a simultaneous format using W40 as the capture antibody and S12 as the detection antibody was selected to maximize sensitivity.

TABLE 2

The Materials used in this assay are as follows

| Reagents/Supplies | Supplier/Manufacturer | Catalog # |
|---|---|---|
| Nunc MaxiSorp ™ 96-well microtiter plates | VWR | 62409-004 |
| PBS 10X stock | JRH Bioscience | 59331-79P |
| Bovine Serum Albumin (BSA) | Intergen | |
| Polyoxyethylene sorbitan monolaurate (Tween 20) | Sigma | P7949 |
| Soluble P-Selectin, truncated P-selectin (tPS) | Centocor Inc. | |
| Horseradish Peroxidase-conjugated Streptavidin (SA-HRP) | Jackson Immuno-research Labs | 016-030-084 |
| Murine mAb W40 IgG | Centocor Inc. | |
| Biotinylated murine mAb S12 IgG | Centocor Inc, | |
| Citric Acid | J. T. Baker | 0118-01 |
| Sodium Phosphate Dibasic | Sigma | S9763 |
| 30% $H_2O_2$ | Sigma | H1009 |
| O-phenylenediamine dihydrochloride (OPD) | Sigma | 8287 |
| B2TT antibody | Centocor Inc. | |
| 4N Sulfuric acid, $H_2SO_4$ prepared from concentrated acid | J. T. Baker | 968102 |

The following buffers were prepared prior to performing the assay:

TABLE 3

Buffers used in Assay

| | |
|---|---|
| 1X PBS | Dilute 10X PBS 1:10 with deionized $H_2O$ |
| PBS/1% BSA | Dissolve 5 grams BSA in 500 ml PBS and filter (0.2 µm) |
| PBS/1% BSA/0.05% Tween 20/25 µg/ml B2TT (azide free) | Dissolve 5 grams BSA in 500 ml PBS; add 0.250 ml Tween 20; Add 1.25 ml B2TT @ 10 mg/ml; and filter (0.2 µm) |
| PBS/0.05% Tween 20 | Add 0.5 ml Tween 20 per liter of PBS and mix thoroughly |
| Citrate/Phosphate Buffer (1 liter) | 4.2 g Citric Acid (20 mM); 7.1 g Sodium phosphate dibasic (anhydrous) (50 mM); Add 900 mls water and adjust pH to 5.0; QS to 1.0 liter with water and filter (0.2 µm). |
| OPD substrate solution (25 mls) | Dissolve three 10 mg OPD tablets in 25 mls citrate/phosphate buffer and add 40 µl 30% $H_2O_2$. Prepare just before use. |
| 4N Sulfuric Acid | Add 20 mls concentrated sulphuric acid to 160 mls deionized $H_2O$. |

Murine W40 $IgG_1$ Purification

Murine W40 $IgG_1$, a murine monoclonal antibody specific for human P-selectin (Johnston, G. I. et al., *J. Biol. Chem.*, 264: 1816–1823 (1989), the teachings of which are incorporated herein by reference in their entirety), was prepared as ascites fluid and was purified by "high salt" protein A chromatography. Ascites fluid was thawed from −70° C. and filtered using several glass prefilters and 0.2 µm membrane syringe filters. The ascites fluid was then adjusted to 3M NaCl with granular sodium chloride and the pH increased to 8.9 by addition of 1M glycine pH 9.6. Protein A Hi-trap columns were equilibrated on a Pharmacia FPLC in MAPS buffer (3M NaCl, 1.5 M glycine, pH 8.9). The ascites fluid, adjusted for salt and pH, was loaded on the Protein A column and flow-through was collected when the $OD_{280}$ rose above baseline. Once sample loading was complete, the column was washed with additional MAPS buffer until the $OD_{280}$ returned to baseline. Bound antibody was first eluted with 0.1M citrate pH 5.5. Collection of eluate was begun and stopped as the $OD_{280}$ rose above and returned to baseline. The pool of eluted antibody was immediately neutralized with the addition of ⅓ final volume 1M Tris, pH 8.0. Other non-W40 IgG proteins bound to the column were removed by washing with 0.1 M citrate pH 3.5. This eluate was also collected and neutralized as described above.

The pH 5.5 eluate was then concentrated using centriplus™ concentrators and dialyzed into PBS using a Slide-A-lyzer™ apparatus (Pierce). Finally the sample was 0.2 µm filtered and the concentration determined by $OD_{280}$.

Murine S12 $IgG_1$ Biotinylation

Murine S12 $IgG_1$ antibody was purified from hybridoma tissue culture supernatant using Protein A Sepharose column chromatography, and was dialyzed into 200 mM $NaHCO_3$, 150 mM KCl, pH 8.5 and concentrated to 3.95 mg/ml for biotinylation. Biotinylation was carried out with a 30:1 molar excess of NHS-LC-biotin (Pierce) to murine S12 IgG. Briefly, mS12 IgG was transferred to a 5 ml polypropylene tube; NHS-LC-biotin was weighed out and quickly reconstituted to 4 mg/ml in DI water. The appropriate amount of NHS-LC-biotin was transferred to the reaction tube containing S12 IgG and mixed at room temperature for 1 hour.

Free biotin was removed from the biotinylated murine S12 IgG antibody by transferring to a Slide-A-lyzer™ for dialysis into PBS. Finally, the antibody was 0.2 µm filtered and the concentration determined by $OD_{280}$.

Truncated P-selectin Generation and Purification

Transfected 293 Tissue Culture Methods

Human 293 kidney cells (ATCC CRL 1573) were obtained from the American Type Culture Collection, 12301 Parklawn Drive, Rockville, Md. 20852, and were transfected with a construct which directs the expression of soluble truncated P-selectin (tPS) from pRC/RSV (Invitrogen) (Ushiyama, S. et al., *J. Biol. Chem.*, 268: 15229 (1993), the teachings of which are incorporated herein by reference in their entirety). Transfectants were cultured in αMEM containing 10% FBS and supplemented with L-glutamine, sodium pyruvate, NEAA and geneticin (G-418) in T-150 flasks. When cells reached confluency, supernatants were decanted, centrifuged to remove cells and debris, and stored at 4° C. for purification.

Truncated P-selectin Affinity Purification

Tissue culture supernatant from 293 cells containing truncated P-selectin (tPS) was collected and pooled for processing. A 25 ml murine G1 affinity column was prepared using the anti-P-selectin murine monoclonal antibody G1 (Geng, J.-G. et al., *Nature*, 343: 757–760 (1990)), and the column was equilibrated with 5 column volumes of 20 mM Tris, 100 mM NaCl, pH 8.3 at 4° C. Tissue culture supernatant was loaded onto the column and flow-through collected. When sample loading was complete, the column was washed with equilibration buffer until the $OD_{280}$ returned to baseline. The affinity column was then washed with 5 column volumes of 20 mM Tris, 1M NaCl, pH 8.3. The column was again equilibrated with 5 column volumes 20 mM Tris, 100 mM NaCl, pH 8.3. Bound tPS was eluted with nine column volumes of 100 mM sodium acetate, 100 mM NaCl, pH 4.1. The column was re-equilibrated in 20 mM Tris, 100 mM NaCl, pH 8.3 containing 0.1% $NaN_3$ and stored for future use.

Eluate fractions were immediately neutralized with 1M MOPS pH 7.9 and concentrated using a Centriplus™ concentrator. Purified tPS was then buffer exchanged into 20 mM MOPS, 100 mM NaCl, pH 7.5 using a Slide-A-lyzer™ apparatus. Finally, the sample was 0.2 µm filtered and concentration determined by $OD_{280}$ extinction coefficient 12.3.

Sandwich ELISA for Detecting Soluble P-Selectin

The sandwich ELISA method for assaying soluble P-selectin levels used the following procedure. Table 4 illustrates the final concentrations of reagents utilized in the sandwich ELISA.

TABLE 4

Final concentrations of reagents used in the ELISA

| Component | Prepare | Final Conc. | Volume added to dilution plate |
|---|---|---|---|
| A1. Sample | 1:2 dilution | 1:4 dilution | 100 µl |
| A2. tPS Standards* | 640 ng/ml–6.4 ng/ml | 320 ng/ml–3.2 ng/ml | 100 µl |
| B. Streptavidin-HRP | (1:25,000) | 1:100,000 | 50 µl |
| C. Biotinylated S12 IgG | 5.0 µg/ml | 1.25 µg/ml | 50 µl |

*A six point standard curve was prepared by serially diluting tPS from 320 ng/ml to 3.2 ng/ml. Serial dilutions were carried out by transferring 66 µl standard into wells containing 100 µl of buffer, mixing and transferring again.

Whole blood (8.5 cc) was collected by venipuncture using a 19-gauge needle in two 10-ml vacutainer tubes containing ACD-A (1.5 cc), heparin or EDTA as anticoagulant. Where the patient had an arterial catheter in place, blood was collected from the in-dwelling arterial line into a plastic syringe containing 1.5 cc ACD-A, heparin or EDTA as anticoagulant. The syringe was filled to the 10 cc mark (8.5 cc draw).

The blood with anticoagulant from the vacutainer or syringe was immediately transferred to a polypropylene centrifuge tube. Platelet poor plasma (PPP) was produced by centrifuging the whole blood for 20 minutes at 1900×g. The PPP was removed from the cell pellet by plastic transfer pipet and was assayed in the ELISA format described below or was aliquoted and frozen at −70° C. for later analysis.

Soluble P-selectin was measured in an enzyme-linked immunosorbent assay (ELISA) by coating 96-well MaxiSor™ (Nunc) microtiter plates with murine anti-P-selectin Mab W40 IgG, by adding 100 µl of antibody (at a concentration of 5 µg/ml in PBS) to each well. Plates were incubated at 4° C. for approximately 18 hours. The coated microtiter plates were washed three times with 200 µl/well of PBS and blocked by the addition of 200 µl/well of PBS containing 1% bovine serum albumin (BSA, Fraction V, Sigma, St. Louis, Mo.) for 1 hour at 37° C. Blocked plates were incubated for 2 hours at 37° C. with the following simultaneously added components: soluble P-selectin standards or donor plasma samples, horseradish peroxidase-conjugated streptavidin and biotin conjugated-anti-P selectin antibody S12 IgG, which binds to a P-selectin epitope which is distinct from that recognized by W40 IgG. PBS containing 1% BSA, 0.05% Tween 20, and 25 µg/ml B2TT (mouse Ig to eliminate non-P-selectin specific human anti-mouse reactivity; Centocor, Malvern, Pa.) was used as the diluent for all assay components. Plasma samples were evaluated at a final concentration of 1:4 in the assay diluent. After incubation of the samples and standards, plates were washed four times with 200 µl/well of PBS with 0.05% Tween 20. Color was developed by the addition of 100 µl/well of the HRP substrate O-phenylenediamine dihydrochloride (OPD). Color development was stopped after 20 minutes by the addition of 100 µl/well of 4N $H_2SO_4$.

Figure 5:
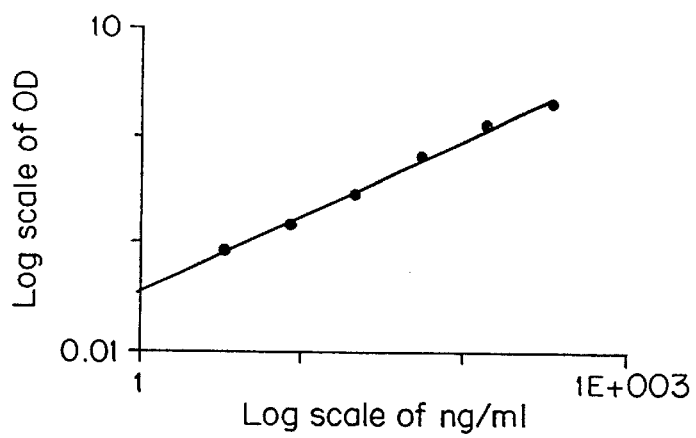
FIG. 5 is a standard curve generated using the soluble P-selectin ELISA described in Example 2 with increasing concentrations (3.2 ng/ml to 320 ng/ml) of recombinantly produced, truncated P-selectin purified from tissue culture supernatant of human kidney cell line 293 transfectants. The assay format used a W40-coated microtiter plate. The standard was added to the plate simultaneously with biotinylated S12 antibody and streptavidin-HRP, and incubated for 2 hours. Color development in the presence of OPD was stopped after 20 minutes with 4N $H_2SO_4$. A correlation coefficient of 0.996 or better was achieved. A log-log fit was chosen as best fit for the data. Inter- and intra-assay precision for the assay is CV<10%.

Plates were read at 490 nM on a Molecular Devices plate reader. Softmax™ software was used to analyze the data. A standard curve was generated by plotting the mean absorbance for known quantities of soluble P-selectin produced by a human kidney cell line (293 cells) transfected with a gene producing a truncated form of P-selectin which does not include the transmembrane portion of the molecule (Ushiyama, S. et al., *J. Biol. Chem.*, 268: 15229 (1993), the teachings of which are incorporated herein by reference in their entirety). FIG. 5 shows a typical standard curve derived from performance of a soluble P-selectin ELISA for concentrations of soluble P-selectin from 3.2 to 320 ng/ml. As seen in FIG. 5, the mean absorbance for each standard value was plotted on the Y-axis and the concentration of P-selectin on the X-axis. The points were fitted using a log-log curve fitting program. The concentration of soluble P-selectin in samples was determined from the standard curve multiplied by the appropriate dilution factor.

Normal levels of endogenous soluble P-selectin were assessed in volunteer donors (n=12) who were not suffering from coronary artery disease. Table 5 shows the normal ranges of soluble P-selectin in serum collected in vacutainers with or without clot-promoting gel and in plasma drawn into the following anticoagulants: ACD-A, heparin, and EDTA.

TABLE 5

Soluble P-selectin Levels in Normal (n = 12) plasma and serum

| Anticoagulant | Plasma P-selectin (ng/mL) | Serum P-selectin (ng/mL) |
|---|---|---|
| ACD | 25.6 ± 7.5 | |
| Heparin | 32.9 ± 7.7 | |
| EDTA | 31.3 ± 6.8 | |
| No Gel | | 73.8 ± 23.6 |
| Gel | | 86.12 ± 23.6 |

Table 5 gives the mean ± standard deviation of soluble p-selectin found in normal donors (n = 12) when the soluble P-selectin ELISA is perfomed on plasma isolated from whole blood collected into the anticoagulants, ACD-A, heparin, or EDTA or on serum collected with or without clot-promoting gel. Soluble p-selectin is considered to be significantly elevated if its value is 3 standard deviations above the normal mean for that particular type of plasma or serum sample.

Performance Characteristics

The intra-assay variability (precision within an assay) for the soluble P-selectin ELISA format was determined by adding known amounts of soluble P-selectin to human plasma which had been collected in ACD-A anti-coagulant. In particular, four plasma samples were spiked with high (600 ng/ml), medium (300 ng/ml), low (40 ng/ml) or no (0 ng/ml) tPS. (The endogenous level of soluble P-selectin in the plasma was considered zero added P-selectin for purposes of this assay.) Twenty-one replicates for each value were determined on the same microtiter plate to derive the intra-assay variability (i.e., each of the four samples was assayed on one plate in replicates of 21).

As shown in Table 6, low, medium, and high amounts of P-selectin were determined in the assay. As indicated in Table 6, a coefficient of variation (CV) less the 10% was achieved for all soluble-selectin levels.

TABLE 6

Intra-assay variability of the soluble P-selectin ELISA for human plasma

| Sample | Zero<br>0 ng/ml spike | Low<br>40 ng/ml spike | Medium<br>300 ng/ml spike | High<br>600 ng/ml spike |
|---|---|---|---|---|
| n | 21 | 21 | 21 | 21 |
| Mean (ng/ml) | 14.0 | 48.0 | 315.7 | 590.8 |
| Std. Dev. | 0.54 | 3.75 | 11.40 | 28.17 |
| CV (%) | 3.8 | 7.8 | 3.6 | 4.7 |

The inter-assay variability (precision between assays) of the soluble P-selectin ELISA format was determined in ten (10) different assays in which six replicate determinations of four plasma samples (ACD-A as anticoagulant) were spiked with zero (endogenous soluble P-selectin only), low (20 ng/ml), medium (250 ng/ml), and high (600 ng/ml) amounts of soluble P-selectin (tPS). As can be observed, all CV's were ≦15% (Table 7).

TABLE 7

Intra-assay variability of the soluble P-selectin ELISA for human plasma

| Sample | Zero<br>0 ng/ml spike | Low<br>20 ng/ml spike | Medium<br>250 ng/ml spike | High<br>600 ng/ml spike |
|---|---|---|---|---|
| n | 10 | 10 | 10 | 10 |
| Mean (ng/ml) | 26.4 | 40.1 | 246.7 | 545.5 |
| Std. Dev. | 2.90 | 2.37 | 11.21 | 29.7 |
| CV (%) | 11.0 | 5.9 | 4.5 | 5.5 |

EXAMPLE 3

Figure 6A:
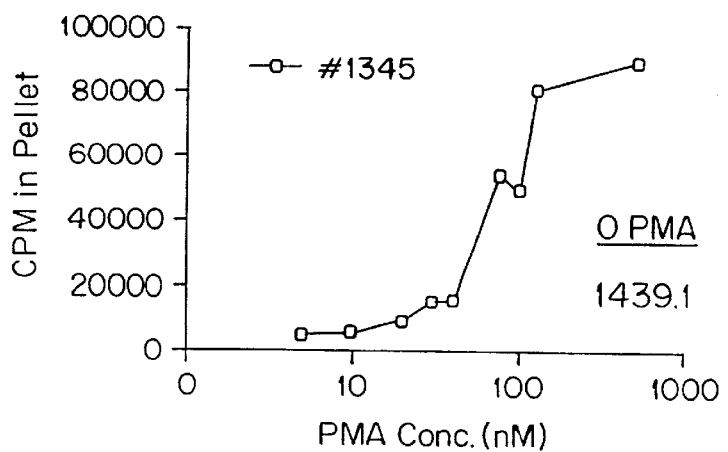
FIGS. 6A–6B are graphs which depict the dose-dependent increase in platelet membrane P-selectin expression determined using a radioimmunoassay (RIA, Example 1).
Figure 6B:
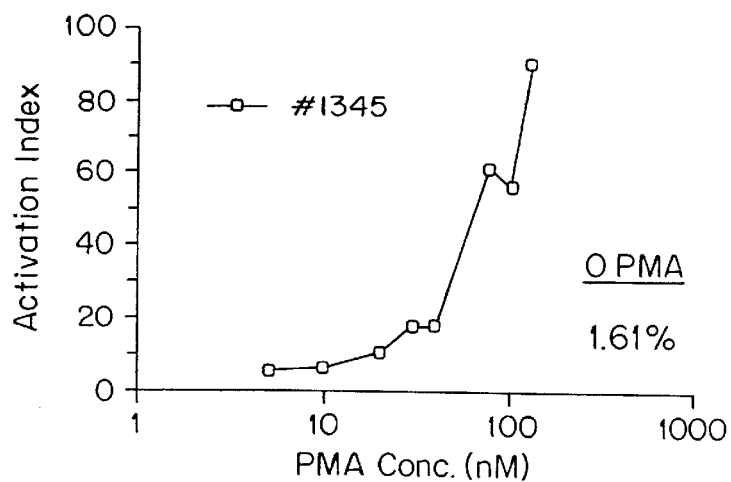

Use of Radioimmunoassay (RIA) to Measure Induction of Expression of Platelet P-selectin in Response to PMA Platelets in plasma from a healthy donor were isolated from whole blood as described in Example 1 and were activated by the platelet activation agonist PMA at various final concentrations ranging from 5 to 500 nM. P-selectin in the activated platelets was translocated to the membrane in response to PMA in a dose-dependent manner which was measured by the binding of the iodinated anti-P-selectin antibody, $^{125}$I-S12. Greater amounts of antibody represented by higher counts per minute were bound with increasing concentrations of PMA. FIG. 6A and FIG. 6B show the results of this titration. In FIG. 6A, the data are presented as counts bound and in FIG. 6B, the Activation Index (AI) for each titration of PMA is calculated according to the formula set forth in Example 1.

EXAMPLE 4

The Use of Flow Cytometry to Measure Membrane Bound P-selectin

Flow cytometry is one method to determine the level of platelet P-selectin and its result contributes to the measurement of the P-selectin profile.

Subpart a) Preparation of Platelet Rich Plasma (PRP) from Whole Blood for the Performance of Flow Cytometry:

Flow cytometry is a method for determining the platelet P-selectin in patient samples, as discussed in this document. The soluble P-selectin was determined using an enzyme-linked immunosorbent assay (ELISA) protocol. Normal values for platelet activation as measured by membrane bound P-selectin and normal levels of circulating soluble P-selectin were determined for apparently healthy volunteer donors.

For in vitro studies, whole blood was collected by venipuncture using a 19-gauge needle into a vacutainer tube containing either ACD solution A (Becton Dickinson, Catalog No 364606) or ACD solution B (Becton-Dickinson, Catalog No 364816) as anticoagulant. Within 30 minutes of the draw, the blood with anticoagulant from one vacutainer was transferred into a 15 mL polypropylene centrifuge tube (VWR, Catalog No 21008-102) containing one premeasured aliquot of apyrase (final concentration 1 U/mL (Sigma, St. Louis, Mo., Catalog No. A 9149) and prostaglandin $E_1$ ($PGE_1$, final concentration 1 $\mu$M) (Sigma, St. Louis, Mo., Catalog No P 5515) in Modified Tyrodes Buffer (MTB) (20 mM HEPES, 187 mM NaCl, 4 mM KCl, 50 mM $Na_2HPO_4$, 1 mM MgCl-6 $H_2O$, 5.5 mM glucose, 1% bovine albumin). The use of polypropylene and the addition of apyrase and $PGE_1$ prevent in vitro platelet activation and stabilize the P-selectin expressed on platelets so that the P-selectin expressed on platelets in the blood sample represents the actual in vivo level of platelet activation. Gentle mixing and handling of the samples and the performance of all procedures at room temperature are also important in preventing in vitro activation. Platelet rich plasma is prepared by centrifuging the whole blood at 600×g in a Beckman GS-6KR centrifuge or equivalent, equipped with a rotor with swinging bucket, with no brake for 3 minutes (blood volumes of 3–6 mL) or 6 minutes (blood volumes of 10 mL) at room temperature. The supernatant platelet rich plasma was removed from each centrifuge tube using a plastic transfer pipette (Sarstedt, No 86.1174 or equivalent) and transferred to a 5 mL polypropylene snap cap tube (VWR, Catalog No 60819-728 or equivalent) and capped to minimize $CO_2$ release.

Subpart b) Processing the Platelet Rich Plasma for Flow Cytometric Analysis:

Platelets in platelet rich plasma are stained with P-selectin specific monoclonal antibodies for flow cytometric analysis. Normal donors have a low percent of activated platelets or platelets which are expressing P-selectin. These normal donors provided samples which were used to determine the level of significant platelet activation. Patient samples show significant platelet activation when the percent of total platelets which are positive for P-selectin is greater than or equal to 2 standard deviations above the mean for the percent positive platelets observed in apparently healthy volunteer donors.

Platelet rich plasma for flow cytometric analysis is diluted 1:6 in Modified Tyrodes Buffer(MTB) and inverted to mix gently. Three stained samples are prepared by aliquoting 45 µL of diluted platelet rich plasma into each of two tubes containing 5 µL of Modified Tyrodes Buffer and one tube containing 5 µL of phorbol 12-myristate 13-acetate (PMA) (Sigma, P-8139 or equivalent) to produce a final concentration of 20 nM PMA. The 20 nM PMA maximally activates the platelet rich plasma during a 15 minute incubation at room temperature and this sample acts as a control to show that the P-selectin specific antibody binds to its ligand in this system. 30 µL of mouse IgG FITC (50 µg/mL, Becton Dickinson, Catalog No. 349041 or equivalent) is added to one of the unactivated tubes containing PRP and buffer. This sample is the negative isotype matched control tube. 30 µL of the fluorescein-conjugated P-selectin specific antibody S12-FITC is added to one non-activated sample (test sample) and to the maximally activated (positive control) samples of diluted PRP. After a 20 minute incubation at room temperature, samples were fixed by the addition of 80 µL of 2% paraformaldehyde (Electron Microscopy Sciences Catalog No 15712-S or equivalent) for 30 minutes at room temperature. Samples were stored at 2–8° C. for up to 72 hours prior to flow cytometric analysis.

Subpart c) Flow Cytometric Analysis of Platelets in PRP:

The prepared samples were analyzed for platelet P-selectin expression using a FACScan™ flow cytometer (Becton Dickinson, San Jose, Calif.). The instrument is equipped with a 15-mW argon-ion laser at a wavelength of 488 nm. The FITC fluorescence is detected using a 530-nm band pass filter. Platelets were identified by their forward and side light scatter on a log scale. The characteristic platelet light scatter was confirmed using a 10E5-FITC antibody to stain the GP IIB/IIIa receptor found on all platelets. A collection gate was drawn around the platelet population and used to collect 10,000 platelets at a rate of 400–1000 events per second. Analysis of the platelet region was performed using CellQuest 40. In the analysis method used, the log FL1 histograms of the control mouse IgG-FITC and the S12-FITC are overlaid. A statistical marker is positioned to result in 1% of the cells stained with the mouse control being considered positive. Keeping the marker in the same position, the percent of S-12-FITC stained cells which are positive for P-selectin expression is determined. The percent positive cells in the maximally activated samples is also assessed to insure that the S12-FITC antibody is binding optimally to P-selectin.

The inventors generated a series of color histograms illustrating the diagnostic sensitivity from the flow cytometry assay shown in FIG. 1. The histograms were not included in the application because they are in color. The purpose of the histogram was to show the linearity of the addition of an increasing percent of fully activated platelets to whole blood containing non-activated platelets. Blood was drawn from a donor and divided into two parts one of which was not activated and the other was activated with PMA. Activated platelets were added to the non-activated sample to increasing percent of the total. The effect of the addition of activated platelets was determined by flow cytometric measurement of the resulting percent positive platelets. In this particular experiment, the basal activation of the non-activated sample is 5.06%. The addition to the non-activated blood sample of maximally activated platelets amounting to 1% of the total number resulted in the detection of 6.41% activated platelets. The addition of 5% activated platelets to the base of 5.06% resulted in 9.39% activation being determined by this method. This experiment shows that the percent of activated platelets present in a sample of whole blood can be accurately assessed with the sensitivity required to make this a viable method for activated platelet determinations.

EXAMPLE 5

The use of a Volumetric Capillary Cytometry System for Measuring Membrane Bound P-selectin The volumetric capillary cytometry system utilized to measure membrane bound P-selectin was the IMAGN2000™ from Biometric Imaging, Mountain View, Calif.

Subpart a) Obtaining and Preparing a Suitable Sample for Measuring Membrane Bound P-selectin Using a Volumetric Capillary Cytometry System:

Whole blood was collected by venipuncture using a 19-gauge needle into a vacutainer tube containing either ACD solution A (Becton Dickinson, Catalog No 364606) or ACD solution B (Becton-Dickinson, Catalog No 364816) as anticoagulant. Within 30 minutes of the draw, the blood with anticoagulant from one vacutainer was transferred into a 15 mL polypropylene centrifuge tube (VWR, Catalog No 21008-102) containing one premeasured aliquot of apyrase (final concentration 1 U/mL (Sigma, St. Louis, Mo., Catalog No. A 9149) and prostaglandin $E_1$ ($PGE_1$, final concentration 1 µM) (Sigma, St. Louis, Mo., Catalog No P 5515) in Modified Tyrodes Buffer (MTB) (20 mM HEPES, 187 mM NaCl, 4 mM KCl, 50 mM $Na_2HPO_4$, 1 mM MgCl-6 $H_2O$, 5.5 mM glucose, 1% bovine albumin). The use of polypropylene and the addition of apyrase and $PGE_1$ prevent in vitro platelet activation and stabilize the P-selectin expressed on platelets so that the P-selectin expressed on platelets in the blood sample represents the actual in vivo level of platelet activation. Gentle mixing and handling of the samples and the performance of all procedures at room temperature are also important in preventing in vitro activation.

Subpart b) Staining a Suitable Sample for Use with Volumetric Capillary Cytometry System:

Whole blood containing apyrase and $PGE_1$ was stained with a cocktail of the P-selectin specific antibodies S12 and W40 which had been labeled with the fluorophore Cy-5 (Amersham-Searle) or APC (Prozyme). Cy5-labeled S12/W40 cocktail 5 µg/mL (10× concentration) in Modified Tyrodes Buffer was kept frozen at −20° C. in 50 µL aliquots. A fresh aliquot was thawed as needed and discarded. To stain platelets for P-selectin, 45 µL of whole blood was aliquoted into an amber tube (Sarstedt Catalog No 72.694.034 or equivalent) containing 5 µL of the S12-Cy5/W40-Cy5 cocktail at a final concentration of each of 0.5 µg/mL and incubated at room temperature for 20 minutes. At the end of the staining incubation, platelets were diluted and fixed by the addition of 1200 µL of 2% paraformaldehyde (Electron Microscopy Sciences Catalog No 15712-S or equivalent).

The stained, fixed, and diluted whole blood sample (40 µL) was placed in the well of a plastic capillary (Catalog No VC120, Biometric Imaging, Mountain View, Calif.) and the fluorescence intensity and number of events within the platelet size gate was determined in the IMAGN2000 instrument (Biometric Imaging, Mountain View, Calif.).

Subpart c) The Total Platelet Count Using the Volumetric Capillary Cytometry System:

The total platelet count in each sample was determined on the IMAGN2000 Biometric Imaging instrument using a Cy-5 labeled CD61 antibody (Becton Dickinson) or a 10E5-Cy5 antibody (Centocor Inc., Malvern Pa.) both of which bind to essentially all platelets. Cy5-labeled CD61 and 10E5 at 5 µg/mL (10×) were stored frozen (−20° C.) in 200 µL aliquots. During use, the reagent is stored at 4° C. Unused refrigerated reagent is discarded monthly. The total platelet count was performed in whole blood by transferring 5 µL of blood to a 12×75 mM polypropylene tube (Falcon 2063 or equivalent) containing 5 mL of Modified Tyrode's Buffer and pipetting up and down twice to complete the 1:1000 dilution. 45 µL of the diluted blood was then added to an amber tube (Sarstedt Catalog No 72.694.034 or equivalent) containing 5 µL of CD61-Cy5 or 10E5-Cy5 (5 µg/mL) and incubated at room temperature for 20 minutes. 40 µL of the diluted blood stained with a pan-platelet marker was placed in the well of a plastic capillary (Catalog No VC120, Biometric Imaging, Mountain View, Calif.) and the fluorescence intensity and number of events within the platelet size gate was determined on the IMAGN2000 instrument (Biometric Imaging, Mountain View, Calif.).

EXAMPLE 6

Use of a Volumetric Capillary Cytometry System to Measurement of Soluble P-selectin The IMAGN2000™ volumetric capillary cytometry system was used to measure soluble P-selectin. The preferred embodiment is using a bead-based format. The sample for this example is prepared in the same way as the sample that was prepared in EXAMPLE 2, discussing the ELISA method of determining soluble P-selectin. Rather than coating a microtiter plate as in EXAMPLE 2, the technician coats the polystyrene beads with the anti-P-selectin antibody, W40. The beads, also called polystyrene sulfated microparticles, (9,7 µm) were passively coated at 0.5× the available particle surface area with the P-selectin specific antibody, W40. The beads were diluted in 30 mM phosphate buffered saline, 1% BSA, 0.01% Tween 20 such that the solids comprised 0.01% of the assay volume. Soluble P-selectin produced by a transfected human kidney cell line (293 cells) was added to the beads in diluent at a range of concentrations. S12-Cy5, a fluorescently labeled anti-P-selectin antibody, was added at a final concentration of 2.5 µg/mL in the assay and incubated with shaking for two hours at room temperature. Rather than putting the microtiter plate in the plate reader as in EXAMPLE 2, the technician places the assay mixture containing the beads in the capillary of the IMAGN2000™ machine. 40 µL of the assay mixture was placed in the well of a plastic capillary (Catalog No VC120, Biometric Imaging, Mountain View, Calif.) and the fluorescence intensity and number of events within the platelet size gate was determined on the IMAGN2000 instrument (Biometric Imaging, Mountain View, Calif.).

EXAMPLE 7

Measurements and Sensitivity of P-selectin in the Presence of a Platelet Agonist Using a Volumetric Capillary Cytometry System The article of manufacture, IMAGN2000™, provides the capability to detect in a sample of whole blood, the number of platelets that are activated and therefore are expressing P-selectin on their surface (membrane). Activated platelets are detected by the addition of a labeled P-selectin specific Mab (in this embodiment a cocktail of S12-Cy5 and W40-Cy5). A fixative is finally added to the whole blood to insure that in vitro platelet activation does not occur. Blood which has been incubated with labeled P-selectin Mab(s) and fixed is then placed into a capillary and a predetermined volume of the blood is scanned by the optical (laser) mechanism of the instrument. A size range that allows for the discrimination of different cell types based on size can be pre-programmed into the instrument. Within the pre-determined size range, every fluorescent event of magnitude sufficiently above background fluorescence is recorded as one event. When whole blood is subjected to increasing concentrations of platelet activation agonist, an increasing number of platelets is activated to the degree that their fluorescence intensity (signal) is sufficiently above background (noise) such that the ratio of signal to noise qualifies them to be counted by the instrument as an event. In a series of experiments performed with the instrument, the platelet activation agonist PMA (phorbol myristate acetate) was added in increasing quantities to whole blood. The results validate the utility of the instrument in assessing the number of activated platelets present in a whole blood sample. In the absence of agonist, four positive event (platelets) were determined to be in the approximately 5 µL of blood diluted 1:25 that was scanned by the laser. At 5 nM PMA, eight activated platelets were detected. At 40 nM PMA 120 activated platelets were detected and at 500 nM PMA 965 activated platelets were counted. The current model of this instrument counts a maximum of 1000 events. In addition to the detection of the number of activated platelets, using a labeled P-selectin specific Mab(s), a second Mab which is specific for a surface molecule common to all platelets (a pan platelet marker) is also added to the whole blood. In this particular embodiment, the marker used is CD61-Cy5. Each platelet will have sufficient CD61-Cy5 on its membrane to be detected as an event (high enough signal to noise ratio). The number of events positive for CD61-Cy5 when adjusted for the volume scanned and the dilution factor of the blood will provide a count of the number of platelets in the whole blood. Dividing the number of events (platelets) positive for P-selectin by the total number of platelets will result in the percent positive platelets. The percent for normal states and for activated platelet states has been established by flow cytometry. The percent positive platelets derived from the current instrument will initially be correlated with a similar calculation derived from flow cytometric determinations on the same sample to establish the substantial equivalence of the two methods.

EXAMPLE 8

Measurement of P-selectin Using a Bead Format in a Volumetric Capillary Cytometry System The article of manufacture, IMAGN2000, provides the capability to detect and quantify the amount of soluble P-selectin present in a sample of platelet poor plasma (PPP). In this embodiment of the assay, 9.7 µM latex beads were coated (covalently or passively) with a P-selectin specific Mab. The coating of the beads was carefully controlled so that a uniform amount of P-selectin Mab was present on each bead. A specified number of beads were incubated in PPP containing soluble P-selectin. Simultaneously with the addition of the beads, a Cy5 labeled P-selectin specific Mab binding to a different site on soluble P-selectin from the site bound by the Mab used to coat the bead, or a Cy5 labeled polyclonal anti-P-selectin antibody preparation is added to the PPP. At the end of the incubation period, the plasma containing the beads is placed in a capillary and a predetermined volume of plasma is scanned by the optical (laser) mechanism of the instrument. A size determination that includes the 9.7 µM beads is pre-set within the program of the instrument. Within that size window, the fluorescent intensity of all events which are sufficiently fluorescent (above background) will be calculated. The fluorescent intensity of the beads will be directly proportional to the amount of soluble P-selectin bound by the surface Mab and detected by the labeled P-selectin antibody(ies). In order to quantify the amount of soluble P-selectin which correlates with a specific fluorescence intensity, a series of beads will be coated with increasing and carefully determined amounts of isolated recombinant soluble P-selectin and then incubated with the Cy5 labeled anti-P-selectin antibody used in the assay. In this way, a standard curve of fluorescence intensity corresponding to soluble P-selectin concentration is established. The amount of soluble P-selectin bound to beads incubated with the test plasma can then be determined from the standard curve solely by determining the fluorescence intensity of the beads. Initial assays with this method show that when known quantities of isolated recombinant soluble P-selectin are spiked into human plasma and incubated with anti-P-selectin Mab (W40) coated beads in the presence of Cy5 labeled S12, the fluorescent intensity of the beads increases linearly with the increased concentration of soluble P-selectin. This method is an alternative way to measure soluble P-selectin that will provide results comparable to the reference method which is the ELISA described in this document.

EXAMPLE 9

Method, Results and Discussion on Platelet and Soluble P-selectin in Patients with Acute Myocardial Infarction After Thrombolytic Therapy and its Relationship to Successful Reperfusion Subpart A: Methods
Controls Ten non-smoking, non-diabetic subjects, aged 21 to 43 years (6 males, 4 females) without a history of bleeding disorders, hypertension, cardiovascular disease, and for at least two weeks free of pharmacologic agent use, were enrolled in the study. All subjects underwent blood sampling after at least 30 minutes of rest and 2 or more hours of fasting. Blood was drawn between 8 and 10 a.m. in order to avoid any diurnal influence and sampled from an antecubital vein, as in the experimental group.

Patients

Twenty three consecutive patients who were admitted to hospital emergency departments with a diagnosis of acute myocardial infarction were included in the study. All patients were enrolled in the randomized trial of RETEPLASE™ (n=13) versus accelerated ALTEPLASE® (n=10) for the treatment of acute myocardial infarction, (GUSTO-III trial). The inclusion criteria were previously reported by the GUSTO Investigators. The GUSTO Investigators, An Int'l Radomized Trial Comparing Four Thrombolytic Strategies for Acute Myocardial Infarction, 329 N. Engl. J. Med. 673, 674 (1993). In summary, patients of any age who presented within 6 hours of symptom onset with more than 30 minutes of continuous symptoms of AMI, and who by 12-lead electrocardiogram had demonstrated at least 1 mM of ST segment elevation in 2 or more limb leads or at least 2 mM ST segment elevation in 2 or more contiguous precordial leads or bundle branch block were included in this trial. Patients were excluded if they had a history of bleeding diathesis, stroke, major surgery or significant trauma in the past six weeks, and hypertension more than 200/110 mM Hg. Patients randomized to RETEPLASE™ therapy received two intravenous 10-MU boluses given 30 minutes apart. Those randomized to ALTEPLASE® received an accelerated dosing regimen: a 15 mg bolus, then 0.75 mg/kg over thirty minutes, then 0.50 mg/kg over one hour. During the baseline sampling every patient had received 325 mg of aspirin, and a least 5,000 U of intravenous heparin. Following the administration of thrombolytic therapy all patients received a continuous infusion of heparin for the first 24 hours as recommended in the GUSTO-III protocol. Id. Blood samples for enzyme-linked immunosorbent assay, and for flow cytometric studies were taken at prespecified intervals: in the emergency department immediately before administration of the thrombolytic therapy and then in the coronary care unit at 3 hours, 6 hours, 12 hours, and finally at 24 hours thereafter. To avoid possible observer bias, blood samples were coded and blinded. Sampling procedures, ELISA, and flow cytometric studies were performed by individuals unaware of the protocol.

Time Course and Exclusion of Blood Samples

The schedule of blood drawing, sample preparation and processing were critical issues of the study design, and were monitored by an independent observer. The actual timing of blood collection for the baseline sample was 9.5±1.4 minutes before the start of thrombolytic therapy; 174.6±21.8 minutes for the 3 hours sample; 371.1±24.2 minutes for 6 hours sample 709.4±17.8 minutes for 12 hours sample; and 1402.9±18.8 minutes for 24 hours sample. Samples were processed within one hour after blood drawing.

Soluble P-selectin

Platelet poor plasma was obtained by centrifugation at +4° C. in a Labofuge at 3000 g for 10 minutes. Samples were stored at −80° C. before final determination. Enzyme-linked immunosorbent essays (ELISA) for P-selectin (Centocor, Inc., Malvern, Pa., USA) were used according to standard techniques. Each sample was measured in duplicate, and the overall intra-assay coefficient of variation was 2.1%±0.3%. Soluble P-selectin levels were assessed as described herein.

Platelet P-selectin

Flow cytometry procedures utilized are described in detail in previously published studies. Ault, K. A., Flow Cytometric Measurement of Platelet Function and Reticulated Platelets, 677 Ann. New York Acad. Sci., 293 (1993); Serebruany, et al., Dietary Coenzyme O10 Supplementation Alters Platelet Size and Inhibits Human Vitronectin (CD51/CD61) Receptor Expression, 29 J. Cardiovasc. Pharm. 16, 17 (1997). Generally, venous blood (8 ml) was collected in a plastic tube containing 2 ml of acid-citrate-dextrose (ACD) (7.3 g citric acid, 22.0 g sodium citrate ×2 $H_2O$ and 24.5 glucose in 1000 ml distilled water) and mixed well. The blood-ACD mixture was centrifuged at 1500 r.p.m. for 10 minutes at room temperature. The upper ⅔ of the platelet-rich plasma (PRP) was then collected and adjusted to pH=6.5 by adding ACD. The PRP was then centrifuged at 3000 r.p.m. for 10 minutes. The supernatant was removed and the platelet pellet was gently resuspended in 4 cc of the washing buffer (10 mM Tris/HCl, 0.15 M NaCl, 20 mM EDTA, pH=7.4). Platelets were washed 4 times in the washing buffer, and an additional 4 times in TBS (10 mM Tris, 0.15 M NaCl, pH=7.4). All cells were then divided into ten plastic capped tubes. Nine portion of washed platelets were incubated with 5 µl fluorescein isothiocyanate (FITC)-conjugated antibodies in the dark at +4° C. for 30 minutes, and one part remained unstained and served as a negative control. Surface antigen expression was measured with monoclonal murine anti-human antibodies: CD9 (p24); CD41a (IIb/IIIa); CD42B (Ib); CD61 (IIIa) (DAKO Corporation, Carpinteria Calif.); CD49b (VLA-2, or Ia–IIa); CD62p (P selectin); CD31 (PECAM-1); CD41b (IIb); and CD51/CD61 (vitronectin receptor)(PharMingen, Inc., San Diego, Calif., USA). After incubation, the cells were washed three times with TBS and resuspended in 0.25 ml of 1% paraformaldehyde. Samples were stored in the refrigerator at +4° C., and analyzed on a Becton Dickinson FACScan® flow cytometer with laser output of 15 mw, excitation at 488 nm, and emission detection at 530±30 nm. The instrument was calibrated daily with fluorescence beads (CaliBRITE®; Becton Dickinson)and measured forward light scatter (mean cell size), side scatter (cellular complexity), and FITC-conjugated fluorescence intensity. Cell size was defined as follows: large-those platelets greater than 48 relative units on the y-axis, medium: between 20 and 48 units, and small: those less than 20 units. All parameters were obtained using four decade logarithmic amplification. The data was collected and stored in list mode, and then analyzed using CELLQuest™ (version 1.2.2) software.

Statistics

A post hoc t-test comparison using the Bonferroni correction was performed to identify specific differences in soluble P-selectin, and platelet receptor expression between AMI patients and controls, and between different time points within AMI groups. A Wilcoxon rank sum test was used to analyze non-parametric data. Normally distributed data are expressed as mean±SEM; and $p > 0.05$ was considered significant. Differences between individual flow cytometric histograms were assessed using the Smirnov-Kolmogorov test incorporated in the CELLQuest™ software.

Subpart B) Results

Eighteen patients were successfully reperfused and remained free of recurrent ischemia in the first twenty four hours of their hospitalization. Three patients (RETEPLASE™-2; ALTEPLASE®-1) had persistent chest pain and ST elevation and later underwent angiography which revealed absence of reperfusion. Two patients (RETEPLASE™-1; ALTEPLASE®-1) developed recurrent ischemia in the first twenty four hours and also underwent emergency angiography.

The clinical characteristics of the AMI patients are shown at Table 8. Patients with failed thrombolysis were. free of alcohol and aspirin use, and where treated later than those in whom thrombolysis was successful. Laboratory data were similar between groups.

TABLE 8

Characteristics of the AMI Patients with the Successful and Failed Thrombolysis.

| | Successful (n = 18) | Failed (n = 5) |
|---|---|---|
| Sex, Male/Female | 15/3 | 3/2 |
| Age, y | 59.4 ± 9.5 | 62.7 ± 8.8 |
| Range | 38–79 | 36–86 |
| Current smoking | 8 | 3 |
| Alcohol use | 6 | 0 |
| Hypertension | 11 | 3 |
| Diabetes | 3 | 2 |
| Prior MI | 2 | 2 |
| Hypercholesterinemia | 8 | 1 |
| Baseline medications: | | |
| Calcium channel inhibitors | 5 | 1 |
| β-blockers | 4 | 0 |
| ACE inhibitors | 1 | 0 |
| Nitrates | 2 | 1 |
| Diuretics | 2 | 0 |
| Aspirin | 7 | 0 |
| MI location: (anterior/inferior) | 14/4 | 3/2 |
| Laboratory data: | | |
| White blood cells, × $10^3$/ml | 8.1 ± 1.4 | 8.0 ± 1.7 |
| Red blood cells, × $10^6$/ml | 3.61 ± 0.6 | 3.88 ± 0.5 |
| Platelets, × $10^3$/ml | 243.2 ± 12.9 | 251.4 ± 14.5 |
| Hemoglobin, g/dL | 15.3 ± 0.6 | 15.5 ± 0.5 |
| Hematocrit, % | 42.8 ± 4.8 | 44.9 ± 4.9 |
| Creatinine, mg/dL | 1.0 ± 0.3 | 1.0 ± 0.4 |

Table 9 summarizes the data on the soluble and platelet P-selectin in AMI patients before and after thrombolytic therapy and in healthy controls. Table 10 contains soluble and platelet P-selectin levels for each patient at the following time points: Baseline, 3 hours, 6 hours, 12 hours, and 24 hours. Table 11 contains the clinical characteristics and outcomes of AMI patients studied.

TABLE 9

A Summary of Soluble and Platelet P-selectin in AMI Patients After Thrombolytic Therapy and Healthy Controls

| Parameter | Baseline | 3 hours | 6 hours | 12 hours | 24 hours |
|---|---|---|---|---|---|
| Patients with successful reperfusion (n = 18) | | | | | |
| Soluble P-selectin | 24.6 ± 2.8$ | 43.4 ± 5.6* | 27.3 ± 1.8 | 27.4 ± 2.2 | 24.0 ± 1.7 |
| Platelet P-selectin | 28.1 ± 1.9 | 27.0 ± 1.1 | 27.9 ± 0.9 | 29.8 ± 1.1 | 30.9 ± 1.1$ |
| Patients with adverse outcomes (n = 5) | | | | | |
| Soluble P-selectin | 28.5 ± 8.1$ | 22.9 ± 5.2[i] | 21.4 ± 5.7 | 26.3 ± 6.7 | 26.1 ± 8.3 |
| Platelet P-selectin | 33.7 ± 1.1[i$] | 34.5 ± 2.3[i$] | 33.8 ± 1.6[i$] | 33.6 ± 1.7[i$] | 35.7 ± 1.8[i$] |

TABLE 9-continued

A Summary of Soluble and Platelet P-selectin in AMI
Patients After Thrombolytic Therapy and Healthy Controls

| Parameter | Baseline | 3 hours | 6 hours | 12 hours | 24 hours |
|---|---|---|---|---|---|
| Controls (n = 10) | | | | | |
| Soluble P-selectin | 11.0 ± 1.4 | | | | |
| Platelet P-selectin | 25.1 ± 2.5 | | | | |

Values are mean ± SEM, and are expressed as ng/ml for soluble form, and log fluorescence intensity for platelet expression;
*$P < 0.05$ versus corresponding baseline measurement;
[i]$P < 0.05$ versus corresponding measurement between groups
[$]$P < 0.05$ versus controls

TABLE 10

Levels of Soluble and Platelet P-selectin
Assessed at Various Time points for Individual Patients

| Patient | Baseline | 3 hours | 6 hours | 12 hours | 24 hours |
|---|---|---|---|---|---|
| 1 F. N., r-PA | | | | | |
| Soluble P-selectin | | | | | |
| Centocor (ng/ml) | 21.89 | 49.10 | 22.52 | 20.71 | 22.60 |
| Bender (ng/ml) | 77.31 | 345.50 | 81.82 | 122.74 | 81.76 |
| Platelet P-selectin | | | | | |
| PharMingen (log fluro) | 30.01 | 30.77 | 31.14 | 32.12 | 34.54 |
| 2. G. L., r-PA | | | | | |
| Soluble P-selectin | | | | | |
| Centocor (ng/ml) | 10.35 | 34.57 | 35.14 | 27.95 | 20.95 |
| Bender (ng/ml) | 37.54 | 156.82 | 147.77 | 152.33 | 102.19 |
| Platelet P-selectin | | | | | |
| PharMingen (log fluro) | 27.75 | 27.08 | 27.64 | 28.89 | 26.60 |
| 3. V. S., t-PA | | | | | |
| Soluble P-selectin | | | | | |
| Centocor (ng/ml) | 27.29 | 17.07 | 17.74 | 18.88 | 21.78 |
| Bender (ng/ml) | 115.94 | 63.65 | 47.79 | 90.97 | 94.45 |
| Platelet P-selectin | | | | | |
| PharMingen (log fluro) | 31.67 | 31.14 | 30.77 | 30.25 | 30.29 |
| 4. A. S., t-PA | | | | | |
| Soluble P-selectin | | | | | |
| Centocor (ng/nl) | 22.14 | 31.57 | 36.70 | 27.93 | 24.31 |
| Bender (ng/ml) | 81.86 | 88.67 | 129.54 | 93.23 | 72.70 |
| Platelet P-selectin | | | | | |
| PharMingen (log fluro) | 22.75 | 20.47 | 23.25 | 22.60 | 25.34 |
| 5. P. L., r-PA | | | | | |
| Soluble P-selectin | | | | | |
| Centocor (ng/ml) | 25.91 | 28.26 | 27.55 | 35.34 | 28.95 |
| Bender (ng/ml) | 52.34 | 143.20 | 102.31 | 188.60 | 156.19 |
| Platelet P-selectin | | | | | |
| PharMingen (log fluro) | 32.31 | 31.92 | 31.10 | 34.05 | 33.97 |
| 6. N. F., r-PA | | | | | |
| Soluble P-selectin | | | | | |
| Centocor (ng/ml) | 17.38 | 23.21 | 17.06 | 29.00 | 13.44 |
| Bender (ng/ml) | 56.81 | 93.24 | 72.76 | 131.85 | 43.49 |
| Platelet P-selectin | | | | | |
| PharMingen (log fluro) | 36.29 | 39.94 | 38.86 | 39.77 | 40.18 |

TABLE 10-continued

Levels of Soluble and Platelet P-selectin
Assessed at Various Time points for Individual Patients

| Patient | Baseline | 3 hours | 6 hours | 12 hours | 24 hours |
|---|---|---|---|---|---|
| 7. H. B., t-PA | | | | | |
| Soluble P-selectin | | | | | |
| Centocor (ng/ml) | 57.24 | 41.55 | 43.51 | 50.18 | 55.93 |
| Bender (ng/ml) | 175.03 | 81.86 | 104.54 | 159.13 | 167.72 |
| Platelet P-selectin | | | | | |
| PharMingen (log fluro) | 36.04 | 40.22 | 36.45 | 41.02 | 39.25 |
| 8. P. O., r-PA | | | | | |
| Soluble P-selectin | | | | | |
| Centocor (ng/ml) | 21.05 | 71.56 | 22.84 | 18.52 | 26.46 |
| Bender (ng/ml) | 15.98 | 154.56 | 38.67 | 55.01 | 38.64 |
| Platelet P-selectin | | | | | |
| PharMingen (log fluro) | 24.65 | 20.06 | 22.12 | 26.64 | 28.04 |
| 9. S. T., r-PA | | | | | |
| Soluble P-selectin | | | | | |
| Centocor (ng/ml) | 9.82 | 10.21 | 9.97 | 10.22 | 9.22 |
| Bender (mg/ml) | 42.51 | 45.07 | 37.55 | 35.02 | 12.58 |
| Platelet P-selectin | | | | | |
| PharMingen (log fluro) | 30.76 | 30.22 | 30.64 | 32.01 | 34.80 |
| 10. F. J., r-PA | | | | | |
| Soluble P-selectin | | | | | |
| Centocor (ng/ml) | 54.37 | 110.70 | 26.35 | 37.49 | 23.16 |
| Bender (ng/ml) | 172.70 | 340.94 | 29.57 | 86.42 | 36.44 |
| Platelet P-selectin | | | | | |
| PharMingen (log fluro) | 37.12 | 35.30 | 34.22 | 37.70 | 38.51 |
| 11. A. H., t-PA | | | | | |
| Soluble P-selectin | | | | | |
| Centocor (ng/ml) | 11.03 | 11.03 | 15.02 | 15.48 | 13.15 |
| Bender (ng/ml) | 27.51 | 28.19 | 42.54 | 40.01 | 32.58 |
| Platelet P-selectin | | | | | |
| PharMingen (log fluro) | 27.32 | 27.01 | 28.81 | 28.44 | 27.70 |
| 12. N. M., r-PA | | | | | |
| Soluble P-selectin | | | | | |
| Centocor (ng/ml) | 19.69 | 25.85 | 21.94 | 17.10 | 24.17 |
| Bender (ng/nl) | 25.08 | 20.54 | 9.25 | 8.84 | 22.76 |
| Platelet P-selectin | | | | | |
| PharMingen (log fluro) | 28.85 | 26.19 | 30.06 | 32.44 | 33.68 |
| 13. F. F., r-PA | | | | | |
| Soluble P-selectin | | | | | |
| Centocor (ng/ml) | 26.99 | 28.93 | 23.56 | 20.65 | 16.66 |
| Bender (ng/ml) | 20.57 | 47.70 | 45.58 | 18.29 | 14.54 |
| Platelet P-selectin | | | | | |
| PharMingen (log fluro) | 27.74 | 26.66 | 25.04 | 27.43 | 30.11 |
| 14. A. X., r-PA | | | | | |
| Soluble P-selectin | | | | | |
| Centocor (ng/ml) | 31.34 | 62.65 | 35.23 | 28.58 | 33.24 |
| Bender (ng/ml) | 54.59 | 179.90 | 50.08 | 29.52 | 37.11 |
| Platelet P-selectin | | | | | |
| PharMingen (log fluro) | 29.34 | 30.47 | 32.18 | 35.33 | 35.70 |

TABLE 10-continued

Levels of Soluble and Platelet P-selectin
Assessed at Various Time points for Individual Patients

| Patient | Baseline | 3 hours | 6 hours | 12 hours | 24 hours |
|---|---|---|---|---|---|
| 15. H. B., t-PA | | | | | |
| Soluble P-selectin | | | | | |
| Centocor (ng/ml) | 15.99 | 21.50 | 15.04 | 20.07 | 12.64 |
| Bender (ng/ml) | 55.13 | 90.44 | 68.87 | 126.14 | 49.95 |
| Platelet P-selectin | | | | | |
| PharMingen (log fluro) | 31.22 | 30.23 | 30.18 | 30.24 | 33.80 |
| 16. K. N., r-PA | | | | | |
| Soluble P-selectin | | | | | |
| Centocor (ng/ml) | 25.13 | 29.83 | 24.38 | 45.79 | 24.27 |
| Bender (ng/ml) | 51.74 | 156.20 | 103.71 | 184.60 | 140.09 |
| Platelet P-selectin | | | | | |
| PharMingen (log fluro) | 33.32 | 33.06 | 32.37 | 36.02 | 37.84 |
| 17. L. P., t-PA | | | | | |
| Soluble P-selectin | | | | | |
| Centocor (ng/ml) | 51.72 | 34.40 | 34.67 | 48.85 | 43.83 |
| Bender (ng/ml) | 166.05 | 80.23 | 105.18 | 146.12 | 171.28 |
| Platelet P-selectin | | | | | |
| PharMingen (log fluro) | 27.05 | 24.14 | 23.29 | 28.29 | 30.03 |
| 18. G. P., r-PA | | | | | |
| Soluble P-selectin | | | | | |
| Centocor (ng/ml) | 17.98 | 61.77 | 20.79 | 22.25 | 27.46 |
| Bender (ng/ml) | 19.94 | 167.60 | 39.15 | 51.06 | 39.44 |
| Platelet P-selectin | | | | | |
| PharMingen (log fluro) | 24.26 | 20.17 | 26.55 | 27.03 | 25.24 |
| 19. K. V., t-PA | | | | | |
| Soluble P-selectin | | | | | |
| Centocor (ng/ml) | 22.66 | 63.93 | 22.49 | 23.62 | 22.98 |
| Bender (ng/ml) | 74.11 | 307.18 | 80.22 | 119.43 | 87.76 |
| Platelet P-selectin | | | | | |
| PharMingen (log fluro) | 31.13 | 32.65 | 32.18 | 34.40 | 34.59 |
| 20. F. U., t-PA | | | | | |
| Soluble P-selectin | | | | | |
| Centocor (ng/ml) | 12.82 | 33.80 | 27.44 | 25.84 | 22.09 |
| Bender (ng/ml) | 38.27 | 127.19 | 111.04 | 132.12 | 100.07 |
| Platelet P-selectin | | | | | |
| PharMingen (log fluro) | 26.31 | 24.40 | 26.17 | 25.20 | 28.84 |
| 21. W. T., r-PA | | | | | |
| Soluble P-selectin | | | | | |
| Centocor (ng/ml) | 30.62 | 22.61 | 18.80 | 23.11 | 30.18 |
| Bender (ng/ml) | 105.24 | 68.80 | 49.21 | 94.66 | 98.17 |
| Platelet P-selectin | | | | | |
| PharMingen (log fluro) | 28.14 | 31.18 | 32.36 | 35.05 | 34.18 |
| 22. T. T., t-PA | | | | | |
| Soluble P-selectin | | | | | |
| Centocor (ng/ml) | 29.51 | 46.94 | 41.97 | 28.09 | 23.64 |
| Bender (ng/nl) | 26.63 | 152.18 | 57.71 | 29.24 | 39.22 |
| Platelet P-selectin | | | | | |
| PharMingen (log fluro) | 22.27 | 19.88 | 20.55 | 21.41 | 22.89 |

TABLE 10-continued

Levels of Soluble and Platelet P-selectin
Assessed at Various Time points for Individual Patients

| Patient | Baseline | 3 hours | 6 hours | 12 hours | 24 hours |
|---|---|---|---|---|---|
| 23. B. B., t-PA | | | | | |
| Soluble P-selectin | | | | | |
| Centocor (ng/ml) | 21.78 | 35.20 | 36.85 | 29.41 | 21.32 |
| Bender (ng/ml) | 86.14 | 89.98 | 118.80 | 90.04 | 70.07 |
| Platelet P-selectin | | | | | |
| PharMingen (log fluro) | 28.04 | 26.11 | 26.24 | 28.78 | 30.02 |

For flow cytometry data - unstained platelets express log fluorescence intensity is 7.5 ± 0.6.

TABLE 11

Clinical characteristics and outcomes of AMI patients

| Patient # | sex | age | smoke | alcohol | ↑BP | DM | Prior MI | ↑Lipids | AMI location | CCI | β-blockers | Aspirin |
|---|---|---|---|---|---|---|---|---|---|---|---|---|
| 1. F. N. | m | 46 | yes | yes | no | no | no | yes | anterior | no | no | no |
| 2. G. L. | m | 51 | no | no | no | no | no | no | anterior | no | no | no |
| 3. V. S. | f | 64 | yes | no | yes | yes | yes | yes | anterior | yes | no | no |
| Failed to reperfuse, emergency PTCA at 30 hours after thrombolysis, 89% LAD stenosis | | | | | | | | | | | | |
| 4. A. S. | m | 66 | no | no | yes | no | no | no | inferior | no | no | yes |
| 5. P. L. | f | 58 | yes | yes | yes | yes | yes | no | anterior | yes | no | yes |
| 6. N. F. | m | 36 | yes | no | no | no | no | no | anterior | no | no | no |
| Recurrent ischemia at 36 hours, PTCA, total block of LCX, CABG, recovery | | | | | | | | | | | | |
| 7. H. B. | m | 71 | no | no | yes | no | yes | no | inferior | no | no | no |
| Failed to reperfuse at 5 hours - PTCA, recovery | | | | | | | | | | | | |
| 8. P. P. | m | 62 | no | no | no | no | no | yes | anterior | no | no | no |
| 9. S. T. | m | 86 | no | no | no | no | no | no | inferior | no | no | no |
| Recurrent ischemia, neck pain, ST elevation, emergency PTCA, triple vessel disease, CABG | | | | | | | | | | | | |
| 10. F. J. | f | 75 | no | no | yes | no | no | yes | inferior | yes | yes | yes |
| 11. A. H. | m | 86 | no | no | yes | no | yes | yes | anterior | no | yes | yes |
| Successfully reperfused, but developed haemorrhagic stroke at 20 hours - now disabled-paraplegia | | | | | | | | | | | | |
| 12. N. M. | m | 38 | yes | yes | yes | no | no | no | anterior | no | no | no |
| 13. F. F. | f | 65 | no | no | yes | yes | no | yes | inferior | yes | no | no |
| 14. A. X. | m | 60 | yes | yes | yes | no | no | no | anterior | no | no | yes |
| 15. H. B. | m | 64 | yes | no | no | no | no | yes | anterior | no | no | no |
| 16. K. N. | m | 49 | yes | yes | no | no | no | no | anterior | no | no | no |
| 17. L. P. | m | 56 | yes | yes | yes | yes | no | yes | anterior | yes | no | yes |
| 18. G. P. | m | 67 | no | no | yes | no | no | no | anterior | no | yes | no |
| 19. K. V. | m | 66 | no | no | no | no | no | no | anterior | no | no | no |
| 20. F. U. | m | 60 | yes | no | yes | no | no | yes | inferior | no | yes | no |
| 21. W. T. | f | 59 | no | no | yes | yes | no | no | anterior | no | no | no |
| Recurrent ischemia, ECG changes 7 hours after thrombolysis, emerg. PTCA, recovery (LAD 95% stenosis) | | | | | | | | | | | | |
| 22. T. T. | m | 66 | no | no | yes | no | no | yes | anterior | yes | no | yes |
| 23. B. B. | m | 46 | no | no | no | no | no | no | anterior | no | no | no |

BP—blood pressure; DM—diabetes; CCI—calcium channel inhibitors

Soluble P-selectin

Figures 7A, 7B:
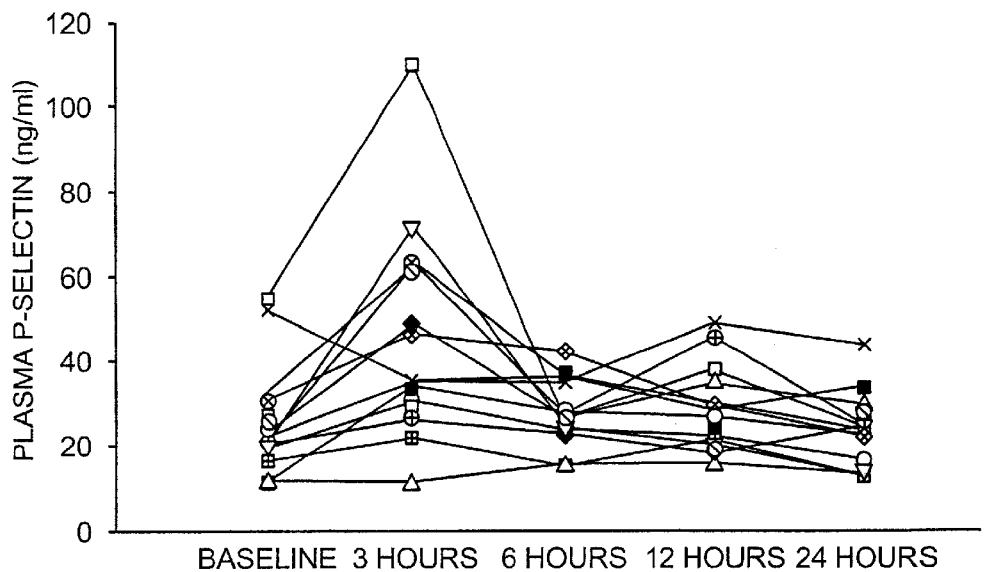
FIGS. 7A and 7B are graphs which illustrate the levels of soluble P-selectin at Baseline, 3 hours, 6 hours, 12 hours and 24 hours after thrombolytic therapy. Each curve represents data from an individual. The data points represent the soluble P-selectin level for each individual patient for the above time points.

Plasma levels of P-selectin were consistently at least twice higher in AMI patients, irrespective of the success of thrombolytic therapy, when compared with healthy controls. A significant increase of plasma P-selectin levels was observed at 3 hours after successful thrombolysis (p=0.002) and was followed by a decrease to the baseline value later at reperfusion. Of the eighteen patients with successful thrombolysis, sixteen experienced an increase in P-selectin levels at 3 hours, and in half of this group the increase was at least two-fold when compared with baseline. In contrast, those patients who failed to reperfuse, expressed high, but flat patterns of soluble P-selectin levels during the first 24 hours after attempted thrombolysis. It should be noted that baseline levels of soluble P-selectin did not differ between the AMI groups. Individual data are presented in FIGS. 7A and 7B.

Platelet P-selectin

Figure 8A:
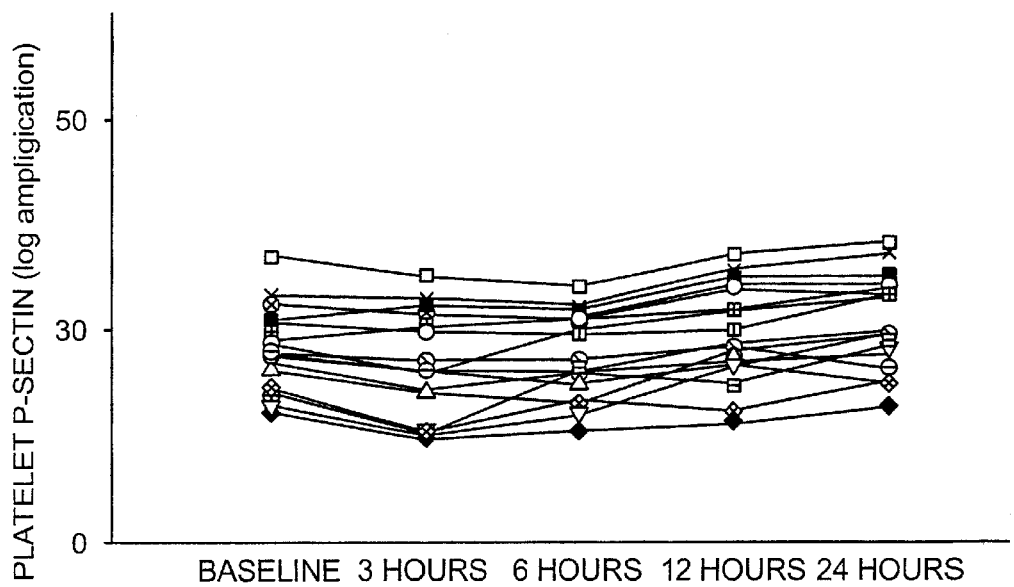
FIGS. 8A and 8B are graphs which illustrate the levels of membrane bound P-selectin at Baseline, 3 hours, 6 hours, 12 hours and 24 hours after thrombolytic therapy. Each curve represents data from an individual. The data points represent the soluble P-selectin level for each individual patient for the above time points.
Figure 8B:
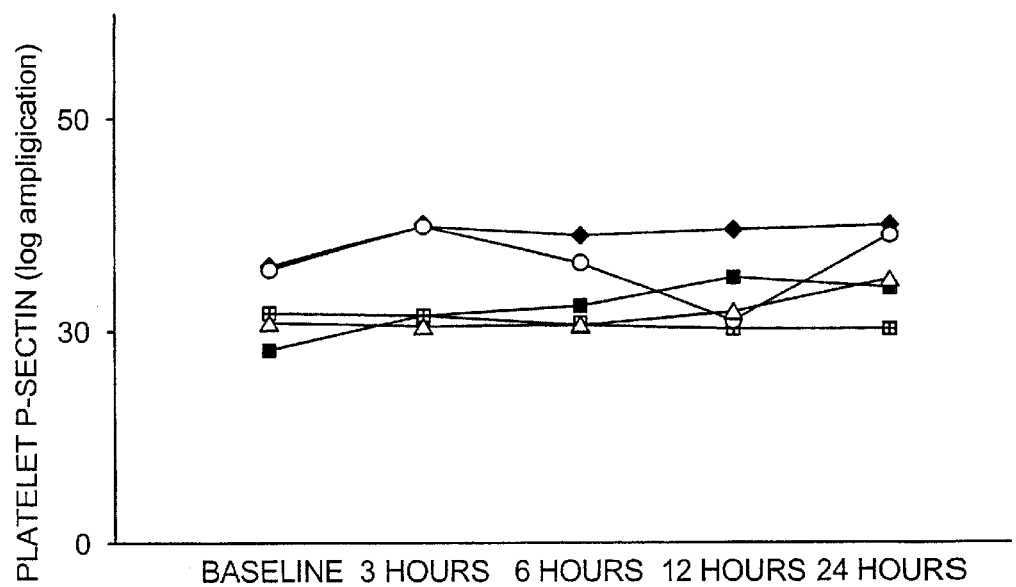

At baseline, before applying any reperfusion strategies, P-selectin exhibit increased expression on the platelet surface of the AMI patients who failed to reperfuse, as compared to successfully reperfused group (p=0.027), and to controls (p=0.01). There were no significant changes of the platelet P-selectin expression within the AMI groups during the first 24 hours after attempted reperfusion, however, platelet P-selectin was higher in patients with failed reperfusion, and this difference was significant at 24 hours (p=0.038). Individual data are presented in FIGS. 8A and 8B.

Subpart C): Discussion

The data from the present study demonstrate that platelet P-selectin is a statistically significant predictor of an unsuccessful course following thrombolytic therapy in patients with acute myocardial infarction. Our study found that increased platelet-bound P-selectin expression was associated with failed coronary thrombolysis, as compared to those patients who were successfully reperfused. Our data are in agreement with another observation that an increased platelet P-selectin expression could represent a possible risk of AMI development in patients with unstable angina. However, the platelet expression of P-selectin in the AMI population in our study was heterogeneous. We have observed similar heterogeneity with other platelet surface receptors including PECAM-1, and glycoprotein IIb/IIIa. In contrast to expectation, we did not note marked platelet P-selectin activation at baseline in the whole AMI population when compared with controls. Whereas certain individuals exhibited a two fold increase in P-selectin, more than half of AMI patients have platelet expression of the P-selectin within the control range.

Another finding reflects the differences between AMI groups occurred early and at 3 hours after attempted reperfusion with the thrombolytic agents. In the successfully reperfused patients, systemic soluble P-selectin levels markedly increased when compared to their own baseline. Conversely, in those patients in whom sustained reperfusion was not achieved, patterns void of this early peak of plasma P-selectin occurred. Taking into account the flat patterns of platelet-bound P-selectin, it is reasonable to speculate that the origin of such a plasma peak is due to release of the endothelial bound fraction of this adhesion molecule. Similar increases of systemic soluble P-selectin early after attacks of vasospastic angina have been observed. Thus, it does not appear that the observed peak of soluble P-selectin is caused by the particular thrombolytic agent, rather it reflects successful reperfusion itself.

In conclusion, the ability to determine predictors of thrombolysis success in AMI can not be overstated. If platelet-leukocyte interactions, and the up-regulation of adhesion molecules are indeed vital elements of the occlusive process, then the degree of systemic activation could affect the response of intravenously administered thrombolytic agents. Increased platelet-bound P-selectin, and lack of the early peak of the soluble P-selectin correlated strongly with unsuccessful coronary thrombolysis in patients presenting with acute myocardial infarction.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method for determining the degree of reperfusion in a patient suffering from a thrombotic event, wherein the patient is subjected to a thrombolytic agent, anti-platelet therapy, a coronary intervention procedure or spontaneous reperfusion, comprising assessing a level of soluble P-selectin in a sample from said patient, said sample comprises blood, plasma or serum, wherein an increase and subsequent decrease of said level is indicative of reperfusion.

2. The method of claim 1, wherein the thrombotic event is selected from a group consisting of myocardial infarction, unstable angina, stroke, pulmonary embolism, transient ischemic attack, deep vein thrombosis, thrombotic re-occlusion subsequent to a coronary intervention procedure, and peripheral vascular thrombosis.

3. A method for determining the degree of reperfusion in a patient subjected to a thrombolytic agent comprising:

a) assessing a level of soluble P-selectin in a patient prior to administering said thrombolytic agent, b) assessing the level of soluble P-selectin in a patient at one or more temporal points subsequent to administering said thrombolytic agent, c) comparing the levels assessed in steps a) and b) and wherein an increase and a subsequent decrease in said level is indicative of reperfusion.

4. The method of claim 3, wherein the thrombolytic agent is selected from a group consisting of a recombinant tissue plasminogen activator, a genetically engineered plasminogen activator, streptokinase, and urokinase.

* * * * *